US011628288B1

(12) United States Patent
Solomon et al.

(10) Patent No.: US 11,628,288 B1
(45) Date of Patent: Apr. 18, 2023

(54) DISINFECTING CAP FOR NEEDLELESS INJECTION SITES

(71) Applicant: Merit Medical Systems, Inc., South Jordan, UT (US)

(72) Inventors: Donald D. Solomon, North Salt Lake, UT (US); F. Mark Ferguson, Salt Lake City, UT (US)

( * ) Notice: Subject to any disclaimer, the term of this patent is extended or adjusted under 35 U.S.C. 154(b) by 327 days.

(21) Appl. No.: 14/797,533

(22) Filed: Jul. 13, 2015

Related U.S. Application Data

(60) Provisional application No. 62/024,162, filed on Jul. 14, 2014.

(51) Int. Cl.
*A61M 39/02* (2006.01)
*A61M 39/16* (2006.01)
*A61M 39/18* (2006.01)
*A61M 39/20* (2006.01)
*A61M 39/10* (2006.01)
*B65D 41/04* (2006.01)

(52) U.S. Cl.
CPC .......... *A61M 39/162* (2013.01); *A61M 39/10* (2013.01); *A61M 39/18* (2013.01); *A61M 39/20* (2013.01); *B65D 41/04* (2013.01)

(58) Field of Classification Search
CPC .......... A61M 39/20; A61M 2005/3104; A61M 2039/1083; A61B 5/15176; F01P 11/0214; B60K 15/0406; B65D 39/084; B65D 2543/00092; B65D 2543/00537; B65D 39/08; B65D 41/04; B65D 41/34; B65D 50/063
See application file for complete search history.

(56) References Cited

U.S. PATENT DOCUMENTS

| 1,744,026 A | 10/1926 | Paltzley |
| 1,868,200 A | 7/1932 | Freedman |
| 2,356,969 A | 5/1942 | Blum |
| 2,299,037 A | 10/1942 | Saueressig |
| 2,351,804 A | 6/1944 | Blum |
| 3,315,830 A | 4/1967 | Flynn |
| 3,431,548 A | 3/1969 | Busler |
| 3,446,596 A | 5/1969 | Salivar et al. |
| 3,976,311 A | 8/1976 | Spendlove |
| 3,987,930 A | 10/1976 | Fuson |
| 4,121,727 A | 10/1978 | Robbins et al. |

(Continued)

FOREIGN PATENT DOCUMENTS

| CN | 205549223 | 9/2016 |
| EP | 0229789 | 7/1987 |

(Continued)

OTHER PUBLICATIONS

European Search Report dated Mar. 6, 2012 for EP08727689.5.

(Continued)

*Primary Examiner* — Bhisma Mehta
*Assistant Examiner* — William R Frehe
(74) *Attorney, Agent, or Firm* — Dorsey & Whitney LLP

(57) ABSTRACT

A female-disinfecting cap and a method for applying the female-disinfecting cap. The cap threadingly accepts a needleless injection site, and applies an antiseptic agent to the needleless injection site. The cap includes a cap body with an opening for accepting the needleless injection site. The cap has an absorbent material that holds an antiseptic agent.

25 Claims, 19 Drawing Sheets

(56) References Cited

U.S. PATENT DOCUMENTS

| | | |
|---|---|---|
| 4,232,677 A | 11/1980 | Leibinsohn |
| 4,299,330 A * | 11/1981 | Walter ................. B65D 41/385 |
| | | 220/288 |
| 4,324,239 A | 4/1982 | Gordon et al. |
| 4,334,551 A | 6/1982 | Pfister |
| 4,344,551 A | 6/1982 | Pfister |
| 4,340,052 A | 7/1982 | Dennehey et al. |
| 4,346,703 A | 8/1982 | Dennehey et al. |
| 4,354,490 A | 10/1982 | Rogers |
| 4,369,781 A | 1/1983 | Gilson et al. |
| 4,402,691 A | 9/1983 | Rosenthal et al. |
| 4,432,764 A | 2/1984 | Lopez |
| 4,432,766 A | 2/1984 | Pellotti et al. |
| 4,440,207 A | 4/1984 | Genatempo et al. |
| 4,450,624 A | 5/1984 | Collier |
| 4,572,373 A | 2/1986 | Johansson |
| 4,597,758 A | 7/1986 | Aalto et al. |
| 4,624,664 A | 11/1986 | Peluso et al. |
| 4,667,837 A | 5/1987 | Vitello et al. |
| 4,671,306 A | 6/1987 | Spector |
| 4,778,447 A | 10/1988 | Velde et al. |
| 4,798,303 A * | 1/1989 | Arnold ................... B65D 41/04 |
| | | 215/329 |
| 4,810,241 A | 3/1989 | Rogers |
| 4,838,875 A | 6/1989 | Somor |
| D303,631 S | 9/1989 | Demarest |
| D310,542 S | 9/1990 | Regnault |
| 4,991,629 A | 2/1991 | Ernesto et al. |
| 5,006,114 A | 4/1991 | Rogers et al. |
| 5,165,559 A * | 11/1992 | Kusz ...................... B65D 41/04 |
| | | 215/216 |
| 5,184,742 A | 2/1993 | Decaprio et al. |
| D333,788 S | 3/1993 | Peschwender |
| 5,190,534 A | 3/1993 | Cendell |
| 5,195,957 A | 3/1993 | Tollini |
| 5,205,821 A | 4/1993 | Kruger et al. |
| 5,242,425 A | 9/1993 | White et al. |
| D340,112 S | 10/1993 | Zeman |
| D341,227 S | 11/1993 | Lang et al. |
| 5,269,771 A | 12/1993 | Thomas et al. |
| 5,385,372 A | 1/1995 | Utterberg |
| 5,439,451 A | 8/1995 | Collinson et al. |
| 5,445,270 A | 8/1995 | Pratz |
| 5,451,113 A | 9/1995 | Lund et al. |
| 5,466,219 A | 11/1995 | Lynn et al. |
| 5,492,147 A | 2/1996 | Challender et al. |
| 5,536,258 A | 7/1996 | Folden |
| 5,554,135 A | 9/1996 | Menyhay |
| 5,593,055 A * | 1/1997 | Repp ....................... B65D 41/17 |
| | | 215/354 |
| 5,620,427 A | 4/1997 | Werschmidt et al. |
| 5,624,057 A | 4/1997 | Lifshey |
| 5,694,978 A | 12/1997 | Heilmann et al. |
| 5,702,017 A | 12/1997 | Goncalves |
| 5,738,663 A | 4/1998 | Lopez |
| 5,792,120 A | 8/1998 | Menyhay |
| 5,839,715 A | 11/1998 | Leinsing |
| 5,894,015 A | 4/1999 | Rechtin |
| 5,951,519 A | 9/1999 | Utterberg |
| 5,954,657 A | 9/1999 | Rados |
| 5,954,957 A | 9/1999 | Chin-Loy et al. |
| 6,045,539 A | 4/2000 | Menyhay |
| 6,152,913 A | 11/2000 | Feith et al. |
| 6,171,287 B1 | 1/2001 | Lynn et al. |
| D456,668 S | 5/2002 | Tse |
| D468,015 S | 12/2002 | Horppu |
| D470,888 S | 2/2003 | Kuboshima |
| 6,523,686 B1 | 2/2003 | Bae |
| 6,695,160 B1 * | 2/2004 | Culley ............... B65D 41/0471 |
| | | 215/44 |
| 6,932,795 B2 | 8/2005 | Lopez et al. |
| 6,960,191 B2 | 11/2005 | Howlett et al. |
| 7,014,169 B2 | 3/2006 | Newton et al. |
| 7,040,598 B2 | 5/2006 | Raybuck |
| 7,040,669 B2 | 5/2006 | Kenmotsu et al. |
| 7,198,611 B2 | 4/2007 | Donnell et al. |
| D545,964 S | 7/2007 | Blanco |
| D547,446 S | 7/2007 | Racz et al. |
| D550,355 S | 9/2007 | Racz et al. |
| 7,282,186 B2 | 10/2007 | Lake, Jr. et al. |
| 7,316,669 B2 | 1/2008 | Ranalletta |
| D573,643 S | 7/2008 | Brigham et al. |
| D607,325 S | 1/2010 | Rogers et al. |
| 7,762,524 B2 | 7/2010 | Cawthon et al. |
| 7,762,988 B1 | 7/2010 | Vitello |
| 7,763,006 B2 | 7/2010 | Tennican |
| 7,780,794 B2 | 8/2010 | Rogers et al. |
| D632,574 S | 2/2011 | Huntington et al. |
| 7,922,701 B2 | 4/2011 | Buchman |
| D639,421 S | 6/2011 | Sano et al. |
| 7,985,302 B2 | 7/2011 | Rogers et al. |
| 8,167,847 B2 | 5/2012 | Anderson et al. |
| 8,172,825 B2 | 5/2012 | Solomon et al. |
| 8,177,761 B2 * | 5/2012 | Howlett ................. A61M 39/20 |
| | | 604/905 |
| 8,197,749 B2 * | 6/2012 | Howlett ............... A61M 39/165 |
| | | 604/905 |
| 8,231,587 B2 | 7/2012 | Solomon et al. |
| 8,231,602 B2 | 7/2012 | Anderson et al. |
| 8,273,303 B2 | 9/2012 | Ferlic et al. |
| 8,328,767 B2 | 12/2012 | Solomon et al. |
| 8,343,112 B2 | 1/2013 | Solomon et al. |
| 8,419,713 B1 | 4/2013 | Solomon et al. |
| 8,523,830 B2 | 9/2013 | Solomon et al. |
| 8,523,831 B2 | 9/2013 | Solomon et al. |
| 8,641,681 B2 | 2/2014 | Solomon et al. |
| 8,647,308 B2 | 2/2014 | Solomon et al. |
| 8,647,326 B2 | 2/2014 | Solomon et al. |
| 8,740,864 B2 | 6/2014 | Hoang |
| 8,784,388 B2 | 7/2014 | Charles et al. |
| 8,808,637 B2 | 8/2014 | Ferlic |
| 8,961,475 B2 | 2/2015 | Solomon et al. |
| 9,079,692 B2 | 7/2015 | Solomon et al. |
| 9,101,750 B2 | 8/2015 | Solomon et al. |
| 9,114,915 B2 | 8/2015 | Solomon et al. |
| 9,242,084 B2 | 1/2016 | Solomon et al. |
| 9,283,369 B2 | 3/2016 | Ma et al. |
| 9,352,140 B2 | 5/2016 | Kerr et al. |
| 2002/0093192 A1 | 7/2002 | Matkovich |
| 2003/0140441 A1 | 7/2003 | Stafford |
| 2003/0153865 A1 | 8/2003 | Connell et al. |
| 2003/0181849 A1 | 9/2003 | Castellanos |
| 2003/0198502 A1 | 10/2003 | Maloney et al. |
| 2004/0039341 A1 | 2/2004 | Ranalletta |
| 2004/0195136 A1 | 10/2004 | Young et al. |
| 2004/0201216 A1 | 10/2004 | Segal et al. |
| 2004/0214316 A1 | 10/2004 | O'Connell |
| 2004/0258560 A1 | 12/2004 | Lake, Jr. et al. |
| 2005/0033267 A1 | 2/2005 | Decaria |
| 2005/0038397 A1 | 2/2005 | Newton et al. |
| 2005/0124970 A1 | 6/2005 | Kunin et al. |
| 2005/0147524 A1 | 7/2005 | Bousquet |
| 2005/0183971 A1 | 8/2005 | Petricca |
| 2005/0203460 A1 | 9/2005 | Kim |
| 2005/0245883 A1 | 11/2005 | Baldwin |
| 2005/0265773 A1 | 12/2005 | De Laforcade |
| 2005/0266714 A1 | 12/2005 | Higgins et al. |
| 2006/0030827 A1 | 2/2006 | Raulerson et al. |
| 2006/0177250 A1 | 8/2006 | Nakagaki |
| 2007/0112333 A1 | 5/2007 | Hoang et al. .................. 604/533 |
| 2007/0202177 A1 | 8/2007 | Hoang |
| 2007/0282280 A1 | 12/2007 | Tennican |
| 2007/0287989 A1 | 12/2007 | Crawford et al. |
| 2007/0293818 A1 | 12/2007 | Stout et al. |
| 2007/0293822 A1 | 12/2007 | Crawford et al. |
| 2008/0019889 A1 | 1/2008 | Rogers et al. |
| 2008/0021381 A1 | 1/2008 | Lurvey et al. |
| 2008/0027399 A1 | 1/2008 | Harding et al. |
| 2008/0033371 A1 | 2/2008 | Updegraff et al. |
| 2008/0038167 A1 | 2/2008 | Lynn |
| 2008/0039803 A1 | 2/2008 | Lynn |
| 2008/0097407 A1 | 2/2008 | Plishka |
| 2008/0086091 A1 | 4/2008 | Anderson et al. |

(56) References Cited

U.S. PATENT DOCUMENTS

| | | | |
|---|---|---|---|
| 2008/0095680 A1 | 4/2008 | Steffens et al. | |
| 2008/0105704 A1 | 5/2008 | Pritchard | |
| 2008/0107564 A1 | 5/2008 | Sternberg et al. | |
| 2008/0132880 A1 | 6/2008 | Buchman | |
| 2008/0147047 A1 | 6/2008 | Davis et al. | |
| 2008/0177250 A1 | 7/2008 | Howlett et al. | |
| 2008/0190485 A1 | 8/2008 | Guala | |
| 2008/0235888 A1 | 10/2008 | Vaillancourt et al. | |
| 2009/0008393 A1 | 1/2009 | Howlett et al. | |
| 2009/0062766 A1 | 3/2009 | Howlett et al. | |
| 2009/0099529 A1 | 4/2009 | Anderson et al. | |
| 2009/0149819 A1 | 6/2009 | Chelak | |
| 2009/0205151 A1 | 8/2009 | Fisher et al. | |
| 2009/0287160 A1* | 11/2009 | Sudo | A61M 5/3134 604/198 |
| 2010/0003067 A1 | 1/2010 | Shaw et al. | |
| 2010/0047123 A1 | 2/2010 | Solomon et al. | |
| 2010/0049170 A1* | 2/2010 | Solomon | A61M 39/165 604/539 |
| 2010/0063482 A1 | 3/2010 | Mansour et al. | |
| 2010/0100056 A1 | 4/2010 | Cawthon et al. | |
| 2010/0242993 A1 | 9/2010 | Hoang et al. | |
| 2010/0306938 A1 | 12/2010 | Rogers et al. | |
| 2010/0313366 A1 | 12/2010 | Rogers et al. | |
| 2011/0044850 A1 | 2/2011 | Solomon et al. | |
| 2011/0054440 A1 | 3/2011 | Lewis | |
| 2011/0064512 A1 | 3/2011 | Shaw et al. | |
| 2011/0064515 A1 | 3/2011 | Ruckey et al. | |
| 2011/0165020 A1 | 7/2011 | Truggvason | |
| 2011/0213341 A1 | 9/2011 | Solomon et al. | |
| 2011/0217212 A1 | 9/2011 | Solomon et al. | |
| 2011/0232020 A1 | 9/2011 | Rogers et al. | 15/246 |
| 2011/0265825 A1* | 11/2011 | Rogers | A61M 39/20 134/166 R |
| 2011/0277788 A1 | 11/2011 | Rogers et al. | |
| 2011/0290754 A1* | 12/2011 | Taber | B65D 41/04 215/329 |
| 2011/0314619 A1 | 12/2011 | Schweikert | |
| 2012/0016318 A1 | 1/2012 | Hoang et al. | |
| 2012/0039764 A1* | 2/2012 | Solomon | A61M 25/0097 422/292 |
| 2012/0039765 A1 | 2/2012 | Solomon | |
| 2012/0082977 A1 | 4/2012 | Rajagopal et al. | |
| 2012/0216359 A1 | 8/2012 | Rogers et al. | |
| 2013/0019421 A1 | 1/2013 | Rogers et al. | |
| 2013/0072908 A1 | 3/2013 | Solomon et al. | |
| 2013/0171030 A1 | 7/2013 | Ferlic et al. | |
| 2013/0197485 A1 | 8/2013 | Gardner et al. | |
| 2013/0299445 A1* | 11/2013 | Cerracchio | B65D 41/0428 215/44 |
| 2014/0001182 A1* | 1/2014 | Wood | B67B 6/00 220/254.1 |
| 2014/0010481 A1* | 1/2014 | Last | B65D 75/5883 383/42 |
| 2014/0135739 A1 | 5/2014 | Solomon et al. | 604/535 |
| 2014/0227144 A1 | 8/2014 | Dickson | |
| 2014/0360968 A1* | 12/2014 | Barth | B65D 47/242 215/44 |
| 2015/0217106 A1 | 8/2015 | Banik et al. | |
| 2015/0231384 A1 | 8/2015 | Ma et al. | |
| 2015/0273199 A1 | 10/2015 | Adams et al. | |
| 2015/0374968 A1 | 12/2015 | Solomon et al. | |
| 2016/0038701 A1 | 2/2016 | White et al. | |
| 2016/0045629 A1 | 2/2016 | Gardner et al. | |
| 2016/0106968 A1 | 4/2016 | Solomon et al. | |
| 2017/0245618 A1 | 8/2017 | Chen et al. | |
| 2019/0099593 A1 | 4/2019 | Avula et al. | |
| 2019/0209781 A1 | 7/2019 | Solomon et al. | |
| 2021/0016077 A1 | 1/2021 | Avula et al. | |

FOREIGN PATENT DOCUMENTS

| | | |
|---|---|---|
| EP | 0462355 | 12/1991 |
| JP | 64002760 | 1/1989 |
| WO | 2004035245 | 4/2004 |
| WO | 2006099306 A2 | 9/2006 |
| WO | 2007097985 | 8/2007 |
| WO | 2008089196 A2 | 7/2008 |
| WO | 2008100950 A2 | 8/2008 |
| WO | 2010002808 A1 | 1/2010 |
| WO | 2010141508 A1 | 12/2010 |
| WO | 2011141508 | 12/2010 |
| WO | 2011053924 A1 | 5/2011 |
| WO | 2011066565 A1 | 6/2011 |
| WO | 2011066586 A1 | 6/2011 |
| WO | 2013184716 | 12/2013 |
| WO | 2015174953 | 11/2015 |

OTHER PUBLICATIONS

European Search Report dated Jun. 20, 2017 for EP10827614.8.
Office Action dated Apr. 22, 2011 for U.S. Appl. No. 12/164,310.
Office Action dated Dec. 23, 2010 for U.S. Appl. No. 12/014,388.
International Search Report and Written Opinion dated Aug. 1, 2008 for PCT/US2008/051087.
International Search Report and Written Opinion dated Aug. 31, 2009 for PCT/US2009/049094.
Notice of Allowance dated Jun. 7, 2017 for U.S. Appl. No. 14/162,207.
International Search Report and Written Opinion dated Jan. 6, 2011 for PCT/US2010/054995.
International Search Report and Written Opinion dated Feb. 7, 2011 for PCT/US2010/058453.
Office Action dated Jan. 27, 2010 for U.S. Appl. No. 12/014,388.
Office Action dated Jun. 9, 2011 for U.S. Appl. No. 12/171,997.
Office Action dated Aug. 16, 2010 for U.S. Appl. No. 12/164,310.
Office Action dated May 5, 2009 for U.S. Appl. No. 12/014,388.
Office Action dated Jun. 21, 2010 in U.S. Appl. No. 12/014,388.
International Search Report and Written Opinion dated Jan. 26, 2011 for PCT/US2010/058404.
Baxa Corporation Launches PadLock Set Saver for IV Safety press release, 2 pages, available at http://www.pr.com/press-release/55432. ,Oct. 10, 2007.
Baxa Corporation Padlock catalog, 3 pages, copyright 2009, available at http://www.baxa.com/SearchResults/ProductDetail/?id-6452BFB9-3048-7B87-701697FB93902BA6.
Baxa Corporation Padlock Microbial Testing Technical Paper, copyright 2007, 4 pages, available at http://www.baxa.com/resources/docs/technicalPapers/PadLockMicrobialChallengeTechPaper.pdf.
Baxa Corporation PadLock Set Saver Specifications and Instructions for Use, copyright 2007, 2 pages, available at http://www.baxa.com/resources/docs/5300103905C.pdf.
BD Q-Syte Luer Access Split Septum product brochure, 4 pages, available at http://www.bd.com/infusion/pdfs/D16333.pdf. ,Nov. 2008.
Braun product catalog, 2pages. ,Aug. 2008.
Curos Port Protector, web page from http://www.iveramed.com/ ,Jul. 11, 2008.
Curos Port Protector product brochure, 2 pages, available at http://www.iveramed.com/clocs/Curos%20Brochure--FINAL.pdf. ,Nov. 2008.
Hospira Male/Female Sterile Cap product packaging insert and brochure, 2 pages. ,Aug. 2004.
Kippmed Vented Non-Vented Female Luer Lock Caps, The KippGroup, ,Jan. 1995 ,2 pgs.
Stoker, et al., One Less Problem, Safe Practices when Administering IV Therapy, Managing Infection Control, 4 pgs ,Jun. 2008.
Tego Connector product brochure, 2 pages, available at http://www.icumed.com/Docs-Tego/M1-1148%20TEG0%20Folder%20Brochure%20Rev.3.pdf. ,Nov. 2008.
Unomedical Medical Products catalog, 2 pages, available at http://www.unomedical.net/au/section05/section10/LocalSSI/..%5C..%5Cpdf%5Cmedical.pdf ,Jan. 2006.
Buchman, et al., A New Central Venous Catheter Cap: Decreased Microbial Growth and Risk for Catheter-Related Bloodstream Infection, The Journal of Vascular Access ,2009 ,11-21.
Maki, et al., In Vitro Studies of a Novel Antimicrobial Luer-Activated Needleless Connector for Prevention of Catheter-belated Blookstream Infection, Clinical Infection Diseases, vol. 50, Issue 12 ,Jun. 15, 2010 ,1580-1587.

(56) References Cited

OTHER PUBLICATIONS

Menyhay, et al., Disinfection of Needleless Catheter Connecors and Access Ports with Alcohol May Not Prevent Microbial Entry: The Promise of a Novel Antiseptic-Barrier Cap, Infection control and Hospital Epidemiology, vol. 27 No. 1 ,Jan. 2006 ,23-27.
Notice of Allowance dated Sep. 1, 2017 for U.S. Appl. No. 14/162,207.
Office Action dated Feb. 27, 2018 for U.S. Appl. No. 14/978,925.
Office Action dated Apr. 4, 2018 for U.S. Appl. No. 14/845,004.
Office Action dated May 25, 2018 for U.S. Appl. No. 15/203,002.
Office Action dated Oct. 20, 2017 for U.S. Appl. No. 15/203,002.
Office Action dated Nov. 17, 2017 for U.S. Appl. No. 14/845,004.
International Search Report and Written Opinion dated Jan. 24, 2019 for PCT/US2018/054202.
International Search Report and Written Opinion dated Feb. 1, 2017 for PCT/US2016/062061.
International Search Report and Written Opinion dated Jun. 22, 2018 for PCT/US2018/014237.
Notice of Allowance dated Sep. 17, 2018 for U.S. Appl. No. 14/845,004.
Notice of Allowance dated Oct. 25, 2018 for U.S. Appl. No. 14/947,341.
Notice of Allowance dated Nov. 9, 2018 for U.S. Appl. No. 15/203,002.
Office Action dated Jun. 7, 2018 for U.S. Appl. No. 14/947,341.
Office Action dated Sep. 14, 2018 for U.S. Appl. No. 14/978,925.
European Search Report dated Jun. 13, 2019 for EP16866954.7.
Office Action dated Jun. 3, 2019 for U.S. Appl. No. 14/978,925.
Office Action dated Aug. 30, 2019 for U.S. Appl. No. 15/797,213.
European Search Report dated Mar. 25, 2020 for EP15808498.8.
Notice of Allowance dated Dec. 19, 2019 for U.S. Appl. No. 15/979,213.
European Search Report dated Jun. 9, 2020 for EP18744486.4.
Office Action dated Jun. 25, 2020 for U.S. Appl. No. 16/235,584.
Office Action dated Oct. 14, 2020 for U.S. Appl. No. 16/150,966.
European Search Report dated Jun. 28, 2021 for EP18865254.9.
Office Action dated Jun. 18, 2021 for U.S. Appl. No. 16/235,584.
Notice of Allowance dated Apr. 6, 2021 for U.S. Appl. No. 16/150,966.
Office Action dated Mar. 8, 2021 for U.S. Appl. No. 16/235,584.
Office Action dated Jan. 5, 2023 for U.S. Appl. No. 16/836,678.

\* cited by examiner

DISINFECTING CAP FOR NEEDLELESS INJECTION SITES

CROSS-REFERENCE TO RELATED APPLICATIONS

This application claims priority from provisional U.S. patent application No. 62/024,162, filed Jul. 14, 2014, entitled, "Disinfecting Cap for Needleless Injection Sites," and naming Donald D. Solomon and F. Mark Ferguson as inventors, the disclosure of which is incorporated herein, in its entirety, by reference.

TECHNICAL FIELD

The present invention relates to caps for medical connectors, and more particularly to caps that can be used to protect the sterility of unconnected medical connectors, such as connectors that may be used for fluid flow or for fluid delivery systems.

BACKGROUND ART

Bloodstream infections, such as may be caused by microorganisms that enter patients via intravascular catheters, are a significant cause of illness and excess medical costs. A substantial number of such infections occur in U.S. intensive care units annually. Additionally, a significant fraction of these infections result in death.

Guidelines from the Centers for Disease Control and Prevention describe various ways to limit bloodstream infections in hospital, outpatient, and home care settings. The guidelines address issues such as hand hygiene, catheter site care, and admixture preparation. However, despite these guidelines, such infections continue to plague healthcare systems at relatively unchanged rates.

Impregnating catheters with various antimicrobial agents is one approach for reducing these infections. Impregnated catheters, however, provide less than satisfactory results. Additionally, some microbes have developed resistance to the various antimicrobial agents used in the catheters. Other systems and approaches have also been developed, but these likewise suffer from a variety of limitations and drawbacks.

SUMMARY OF THE EMBODIMENTS

In accordance with one embodiment of the invention, there is provided a female-disinfecting cap for threadingly accepting a needleless injection site and applying an antiseptic agent to the needleless injection site. In this embodiment, the cap includes a cap body having an inner sidewall defining a chamber having an opening for accepting the needleless injection site. The sidewall has a piloting zone devoid of threads and immediately adjacent to the opening. The piloting zone has a first diameter. The sidewall also has an initial threading zone immediately adjacent to the piloting zone. The initial threading zone has a first diameter. The sidewall also has a transition zone immediately adjacent the initial threading zone. The transition zone has a transitioning diameter. The sidewall also has a main zone immediately adjacent the transition zone. The main zone has a second diameter. The second diameter is less than first diameter. The transitioning diameter changes from the first diameter, at the point where the transition zone contacts the initial threading zone, to the second diameter at the point where the transitioning zone contacts the main zone. In some embodiments, the cap also includes an absorbent material for holding the antiseptic agent disposed in the chamber. The cap also includes a pair of threads that protrude from the sidewall and extend from the initial threading zone, through the transition zone and into the main zone, but do not extend into the piloting zone.

Preferably, in some embodiments the first diameter is between 0.31 inches and 0.32 inches inclusive.

In a preferred embodiment, the first diameter is between 0.314 inches and 0.316 inches inclusive. In a further preferred embodiment, the first diameter is 0.315 inches.

In a preferred embodiment, the pilot zone extends from the opening to a depth of between 0.02 inches to 0.03 inches inclusive.

In another preferred embodiment, the pilot zone extends from the opening to a depth of between 0.024 inches to 0.026 inches inclusive. Preferably, the pilot zone extends from the opening to a depth of 0.025 inches.

In another preferred embodiment, the first diameter extends from the opening to a depth of 0.057 inches to 0.067 inches inclusive. Preferably, the first diameter extends from the opening to a depth of between 0.061 inches to 0.063 inches inclusive. Preferably, the first diameter extends from the opening to a depth of 0.062 inches.

In another preferred embodiment, the initial threading zone extends from the end of the pilot zone to a depth of 0.057 inches to 0.067 inches inclusive from the opening. Preferably, the initial threading zone extends from the end of the pilot zone to a depth of 0.062 inches from the opening. Preferably, the transition zone begins at a depth of 0.057 inches to 0.067 inches from the opening inclusive and extends to a depth of 0.075 inches to 0.125 inches inclusive. Also preferably, the transition zone begins at a depth of 0.062 inches from the opening and extends to a depth of 0.100 inches from the opening.

In a preferred embodiment, the second diameter is between 0.298 inches and 0.302 inches inclusive. Preferably, the second diameter is 0.3 inches.

In other embodiments, the threading, has a radial height sufficient to define an inner threading diameter of between 0.287 inches and 0.291 inches inclusive. Optionally, the threading has a radial height sufficient to define an inner threading diameter of not less than 0.287 inches.

In related embodiments, the threading has a width, in the longitudinal direction of the cap, of between 0.020 inches and 0.025 inches inclusive.

In other embodiments, the cap further includes the antiseptic agent.

In other embodiments, the cap further includes a gripping portion.

Also, in other embodiments, the cap further includes a cover disposed over the opening of the chamber. Optionally, the cover includes an impervious pliable material.

In one embodiment, a method is provided for applying a female-disinfecting cap and applying an antiseptic agent to a needleless injection site. The method includes placing a cap having a pilot zone over the needleless injection site. The pilot zone turns freely on the needleless injection site without interference form the diameter of the pilot zone. The method also includes engaging the threads of the needleless injection site in a thread starting zone. The thread starting zone also turns freely on the needleless injection site without interference at the diameter of the zone, and further without interference from the threads of the cap. The thread starting zone has the same diameter as the pilot zone. The method further includes turning the cap once the threads have engaged the threads of the needleless injection site so as to draw the needleless injection site into a transition zone in which the diameter progressively reduces from the diameter of the pilot and thread starting zones and the diametric fit of the needleless injection site at the outer diameter of the transition zone begins to interfere with the outer diameter of the threads of the needleless injection site, so as to create an interference acting to retain the cap to the needleless injection site and to resist unintended rotation and removal of the cap during use. Optionally, the cap is turned further on the needleless injection site further drawing the needleless injection site into a main zone of the cap in which the outer diameter of the main zone further interferes with the outer diameter of the threads of the needleless injection site.

BRIEF DESCRIPTION OF THE DRAWINGS

The foregoing features of embodiments will be more readily understood by reference to the following detailed description, taken with reference to the accompanying drawings, in which:

In FIG. 19, the user is seen to have grasped with one hand a graspable end of the connector cap while with another hand to have grasped the carrier;

In FIG. 20, the user has partially removed the cap from its corresponding hole in the carrier and caused some of the cover portion of the sealing tab to be removed from the openable end of the cap; and In FIG. 21, the user has complete removed the cap from its corresponding hole in the carrier and caused the cover portion of the sealing tab to be removed from the openable end of the cap.

DETAILED DESCRIPTION OF SPECIFIC EMBODIMENTS

Figure 1:
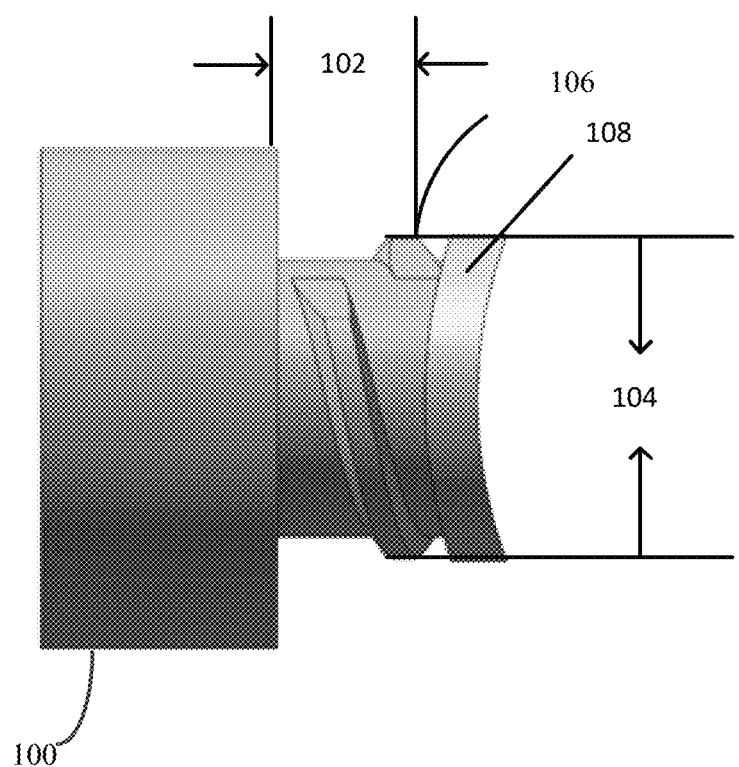
FIG. 1 shows a side view of a prior-art Q-Syte Needleless Injection Site.

Disclosed herein are caps that can be used to protect and/or disinfect medical connectors. Systems and methods related to such caps are also disclosed. A medical connector cap is a cap for a medical connector, such as (but not limited to) a luer connector. A "female medical connector cap" is a cap for a female medical connector. A "male medical connector cap" is a cap for a male medical connector. The cap may, but need not necessarily, include a disinfectant. The cap may, but need not necessarily, be capable of cleaning or disinfecting the medical connector for which it is a cap.

An example of medical connectors for which caps disclosed herein may be used are intravascular connectors associated with a fluid pathway, such as an IV line. Commonly, a fluid pathway is used to intermittently administer medications to a patient. For example, a fluid pathway, which communicates fluids with a patient's blood stream, may have one or more connectors associated therewith. Each of the fluid pathway connectors can be connected to other connectors, such as a connector associated with a central line. In such a situation, the medical connectors, such as luer lock connectors, are connected and disconnected at various times, and may remain disconnected for several minutes or hours. Medical connector caps are used to cover and protect the various medical connectors while the connectors are separated from one another. When the medical connectors are separated from each other, there are two connectors that each can benefit from being covered by a cap. Therefore, in some cases, it can be advantageous to have a single connector set that can be used to provide protection for both ends of a separated connection. In other or further embodiments, a cap can include an antiseptic for disinfecting a medical connector. In some cases, it can be advantageous for the cap to form a seal with the medical connector to thereby prevent the antiseptic from exiting the cap into the fluid pathway.

In some embodiments, the medical connector comprises a needleless injection site, which may sometimes be referred to as a needleless injection port, hub, valve, or device, or as a needleless access site, port, hub, valve, or device, and which can include such brands as, for example, Clave® (available from ICU Medical, Inc.), SmartSite® (available from Cardinal Health, Inc.), and Q-Syte™ (available from Becton, Dickinson and Company). Stated otherwise, in some embodiments, the cap can be suitably connected with any of a variety of different needless injection sites, such as those previously listed. In certain embodiments, once cap has been applied to or coupled with connector, it is unnecessary to disinfect (e.g. treat with an alcohol swab) the connector prior to each reconnection of the connector with another connector, as the connector will be kept in an uncontaminated state while coupled with the cap. Use of the cap thus can replace the standard swabbing protocol.

Needleless Injection Sites (NIS) are intended to be compliant with the ISO luer thread standard (ISO 594-2), but vary dimensionally, even within the standard. The ISO standard does not anticipate mating caps that lack a luer post—such as disinfecting caps. The problem is providing a secure fit which will not become loose with time and use. In a standard luer connection, the securement is provided by the locking taper fit of the male luer post in the female luer. In a disinfecting cap for an NIS, there is no luer post, and the securement must be provided by other features. In the design presented herein, and the securement may be provided by slight interference between an inner diameter of the cap, and an outer diameter of the NIS. For example, major thread diameter of the cap and the major thread diameter of the NIS may provide the interference fit, as discussed in more detail below.

The challenge is providing a fit which has sufficient interference to provide security in use, but not so much interference as to be difficult to install. This is complicated by the dimensional variation in the range of NIS brands and models on the market. There are many different brands of NISs in the marketplace, and disinfecting caps should attach to each of the various available models securely. Otherwise, a disinfecting cap may be able to be secured on some NISs but not others.

FIG. 1 to FIG. 4 show side views of prior-art NISs 100, 200, 300 and 400 respectively. In accordance with preferred embodiments of the present invention, methods and apparatus are disclosed for a disinfecting cap for a variety of NISs. As can be seen from FIG. 1, FIG. 2, FIG. 3 and FIG. 4, as well as Table 1, NISs vary in their dimensions.

TABLE 1

NIS Dimensions

| NIS | Major Diameter (in) | Longitudinal Distance To First Point of Thread Interference Fit With CCI Cap (in) |
| --- | --- | --- |
| MicroClave | 0.302 | 0.170 |
| MicroClave Clear | 0.305 | 0.173 |
| Clave | 0.303 | 0.170 |
| MaxPlus, MaxPlus Clear | 0.306 | 0.185 |
| SmartSite | 0.307 | 0.203 |
| SmartSite Plus | 0.304 | 0.137 |
| Ultrasite | 0.301 | 0.220 |
| B-Braun | 0.302 | 0.240 |
| Q-Syte | 0.303 | 0.134 |

Two NISs that pose particular problems for securely attaching disinfecting caps are the Q-Syte NIS 100 and some versions of the SmartSite NIS 200. These two models, the Q-Syte NIS 100 and the SmartSite NIS 200, show the wide dimensional variation among NISs. Some embodiments of the present invention provide a secure fit which does not allow the cap to fall off the NIS during normal use and wear. Some embodiments prevent damage to a septum 108 of the Becton Dickinson Q-Syte NIS 100. Some embodiments provide the previously mentioned functions on a range of NIS brands and models.

FIG. 1 shows a side view of the prior-art Q-Syte NIS 100. Of the above mentioned NISs, the Q-Syte NIS 100 has the shortest longitudinal distance 102 to the first point of thread interference 106 with a disinfecting cap. Specifically, the Q-Syte NIS 100 has a longitudinal distance 102 of 0.134". The Q-Syte NIS 100 also has a major thread diameter 104 of 0.303". The Q-Syte may be unique from other caps in that the septum 108 (also referred to as an elastomeric valve) extends radially outward in a "flange" like shape. In other NISs, the elastomeric valve may be captured inside a bore in the NIS.

Figure 2:
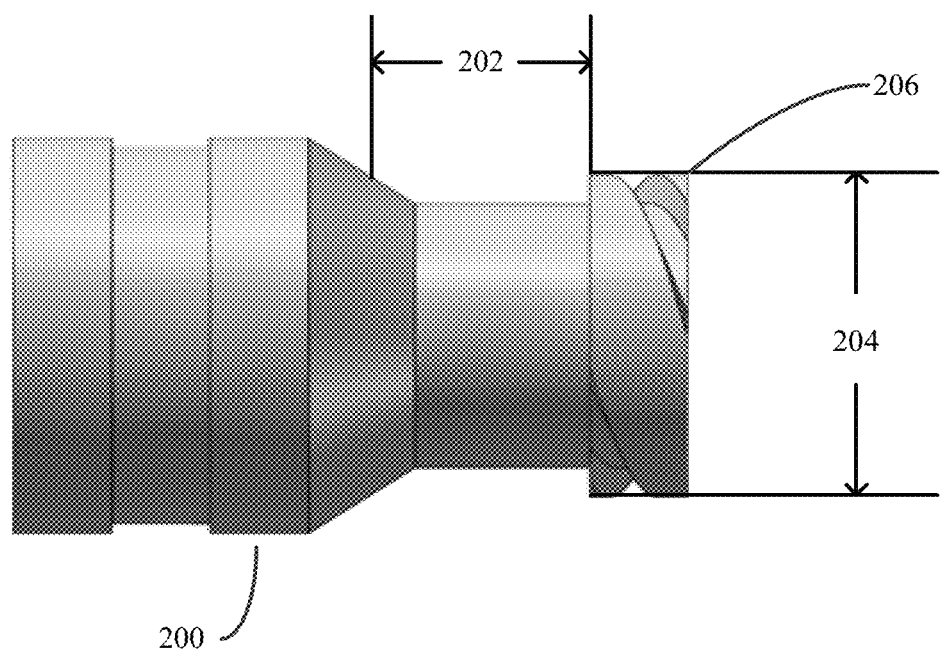
FIG. 2 shows a side view of a prior-art SmartSite Needleless Injection Site.

FIG. 2 shows a side view of a prior-art SmartSite NIS 200. By comparison, the SmartSite NIS 200 has the longest longitudinal distance 202 to the first point of thread interference 206 with a CCI cap of the above mentioned NISs. Specifically, the SmartSite NIS 200 has a longitudinal distance 202 of 0.203". The SmartSite NIS 200 has a major thread diameter 204 of 0.307".

Figure 3:
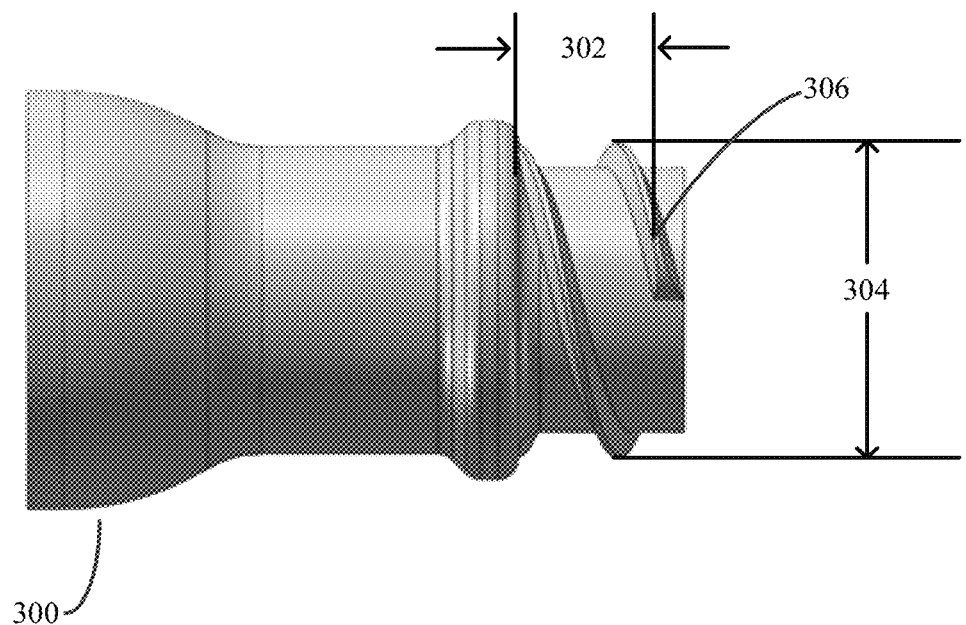
FIG. 3 shows a side view of a prior-art SmartSite+ Needleless Injection Site.
Figure 4:
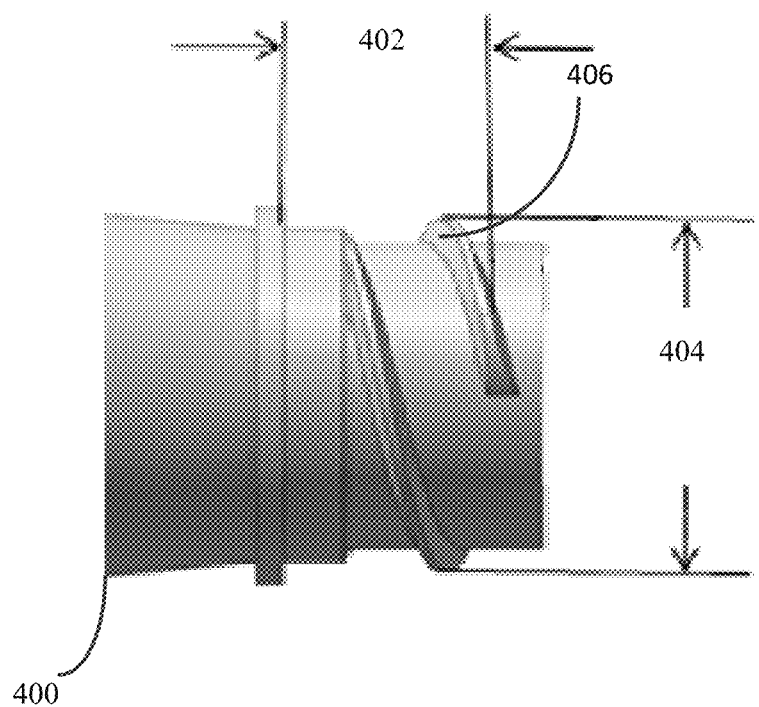
FIG. 4 shows a side view of a prior-art ICU MicroClave Clear Needleless Injection site.

Two other examples of NISs 300 and 400 are shown in FIG. 3 and FIG. 4, respectively. FIG. 3 shows a side view of prior-art SmartSite+ NIS 300. SmartSite+ NIS 300 has an intermediate longitudinal distance 302 to the first point of thread interference 306 with a CCI cap. Specifically, the SmartSite+ NIS 300 has a longitudinal distance 302 of 0.137". The SmartSite+ NIS 300 has a major thread diameter 304 of 0.304".

FIG. 4 shows a side view of prior-art ICU MicroClave Clear NIS 400. ICU MicroClave Clear NIS 400 has an intermediate longitudinal distance 402 to the first point of thread interference 406 with a CCI cap. Specifically, the ICU MicroClave Clear NIS 400 has a longitudinal distance 402 of 0.173". The ICU MicroClave Clear NIS 400 has a major thread diameter 404 of 0.305".

Figure 5:
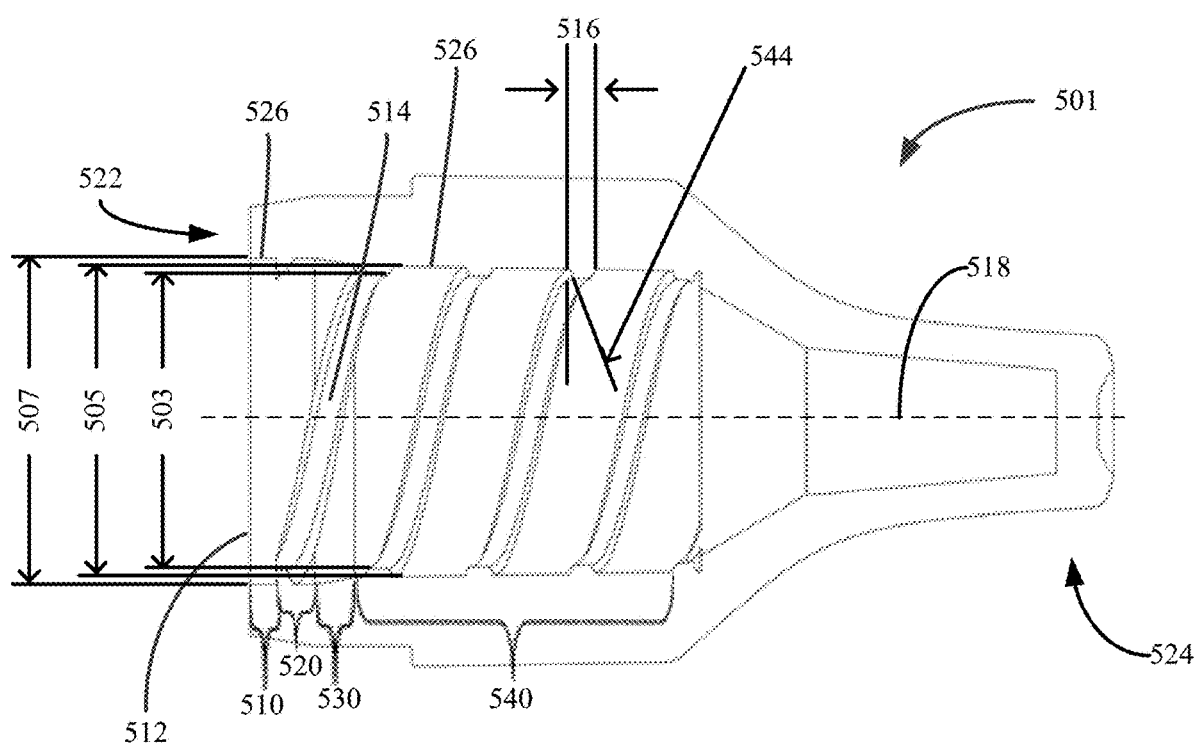
FIG. 5 shows a sectional view of a preferred embodiment of the invention.

FIG. 5 shows a sectional view of a preferred embodiment of the invention. A medical connector cap 501 may have an openable end 522 that is open to a cavity into which the medical connector is received. In some embodiments, the cap 501 may be referred to as a female medical connector cap. Typically, prior to use, the openable end 522 of the medical connector cap 501 is covered to prevent contamination of the interior of the cap 501, and for that reason we term this end as "openable" rather than "open". The cap 501 also has a graspable end 524 that is the end of the cap 501 that is grasped by a user in placing the cap 501 on a medical connector, and in removing the cap 501 from the medical connector. We refer to the graspable end 524 as "closed" because the cavity of the medical connector cannot be reached from the graspable end in some embodiments of the invention.

The cap 501 has a new bore and thread design with the following features: a Piloting Counter bore (Zone 1) 510 having a Counter Bore first diameter 507 at the opening 512 of the cap 501 to provide centering of the cap 501 over the mating NIS prior to and during starting engagement of the threads 514 of the cap 501. (This Zone 1 510 may be referred to as a piloting zone 510.)

Following the pilot counter bore (Zone 1) 510 there is a free running zone (Zone 2) 520 in which the cap threads 514 are allowed to begin threading engagement of the threads of a medical connector without resistance. (This Zone 2 520 may be referred to as an initial threading zone 520.)

The thread width 516 (in all zones 510, 520, 530 and 540) is sized in the longitudinal direction 518 to easily engage a range of mating NIS models without interference in the longitudinal direction 518.

A minor diameter 503 of the thread 514 (in all zones 510, 520, 530 and 540) is sized to prevent pinching—and associated damage—of the Q-syte silicone septum 108. See FIG. 1.

A second diameter 505 of the main bore (Zone 4) 540, also referred to as the cap major thread diameter 505, is sized diametrically to provide thread 514 locking interference with a range of NISs. This second diameter 505 is carefully specified to maintain an ease of engagement as well. (This Zone 4 540 may be referred to as a main zone 540.) In some embodiments, side walls 526 of the main bore 540 may have a taper. In a preferred embodiment, each wall of the main bore 540 may have a taper of approximately 1 degree relative to the longitudinal axis 518. However, in other embodiments, the walls 526 of the main bore 540 may not be tapered.

Between the Piloting Counter bore 510 and Main Bore 540, a ramp or taper Transition (Zone 3) 530 is provided. In the taper zone 530 the diameter of the side wall 526 tapers between the bore first diameter 507 and the second diameter 505. The angle of the transition is chosen to balance the need for a rapid transition in bore with the need for the increase in resistance to installation occurring at the transition to be gentle. (This Zone 3 530 may be referred to as a transition zone 530.) In some embodiments, and in particular with some NISs, the inner diameter of the transition zone 530 may provide the interference fit with the medical connector. For example, in some embodiments, the threads of the medical connector may have an interference fit with the inner diameter of the cap in the transition zone 530.

A set of preferred dimensions for embodiments of the invention which work with a range of NIS dimensions are shown in Table 2:

TABLE 2

Range of dimensions for preferred embodiments of invention

| Zone 1: Pilot Counter Bore 510 | |
|---|---|
| First Diameter 507: | .310" to .320" (.315" preferred) |
| Counter Bore Depth 510: | .020" to .030" from opening 512 of cap 501 (.025" Preferred) |
| Zone 2: Free Running Zone 520 | |
| Diameter: | Same as Zone 1 pilot counter bore 510 first diameter 507 |
| Depth 520 | .057" to .067" from opening 512 of cap 501 (.062" preferred) |
| Zone 3: Transition Zone 530 | |
| Diameter: | May transition from Zone 2 pilot bore first diameter 507 to Zone 4 main bore 540 second diameter 505 in a straight or near straight line |
| Ending Depth: | .075" to .125" from opening 512 of cap 501 (.100" preferred) |
| Zone 4: Main Bore 540 (Thread Locking Zone) | |
| Second Diameter 505: | .298" to .302" |
| Threads: Zone 2 through Zone 4 | |
| Thread Minor Diameter 503: | .287" to .291" In particular, the Minor Diameter 503 should not be smaller than .287" to prevent damage to the Q-Syte septum 108. |
| Thread Width 516 at the Minor Diameter 503: | .020" to .025" (.021" Preferred) |
| Thread angle 544: | The threads can be straight sided or angled up to 30 degrees (25 degrees preferred). See Fig%. 5. |

Figure 6:
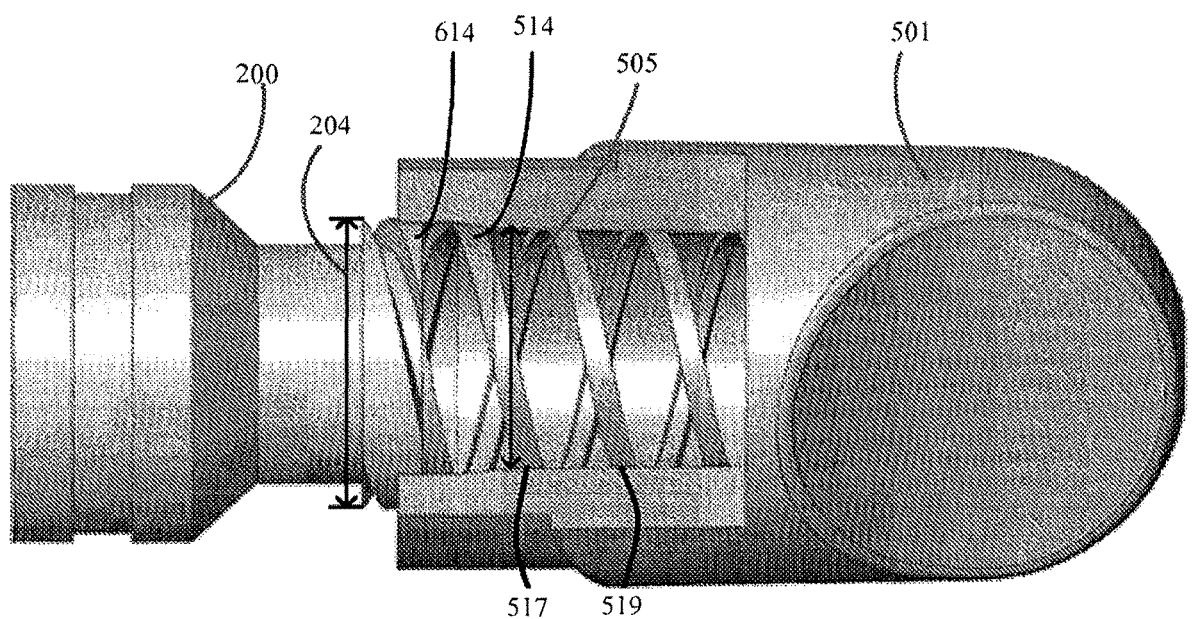
FIG. 6 shows a partial cut-away view of a preferred embodiment of the invention beginning to engage a NIS.

FIG. 6 shows a partial cut-away view of a preferred embodiment of the cap 501 of the present invention beginning to interact with prior-art SmartSite NIS 200. As shown, the NIS threads 614 have not threadingly engaged the first thread 517 and/or the second thread 519 of the cap threads 514. The NIS 200 has entered the pilot counter bore 510. As discussed, the pilot counter bore 510 centers the cap 501 over the mating NIS 200 prior to and during engagement of the cap threads 514. Once the NIS has been centered with the counter bore 510, it may begin to threadingly engage the cap threads 514.

Figure 7:
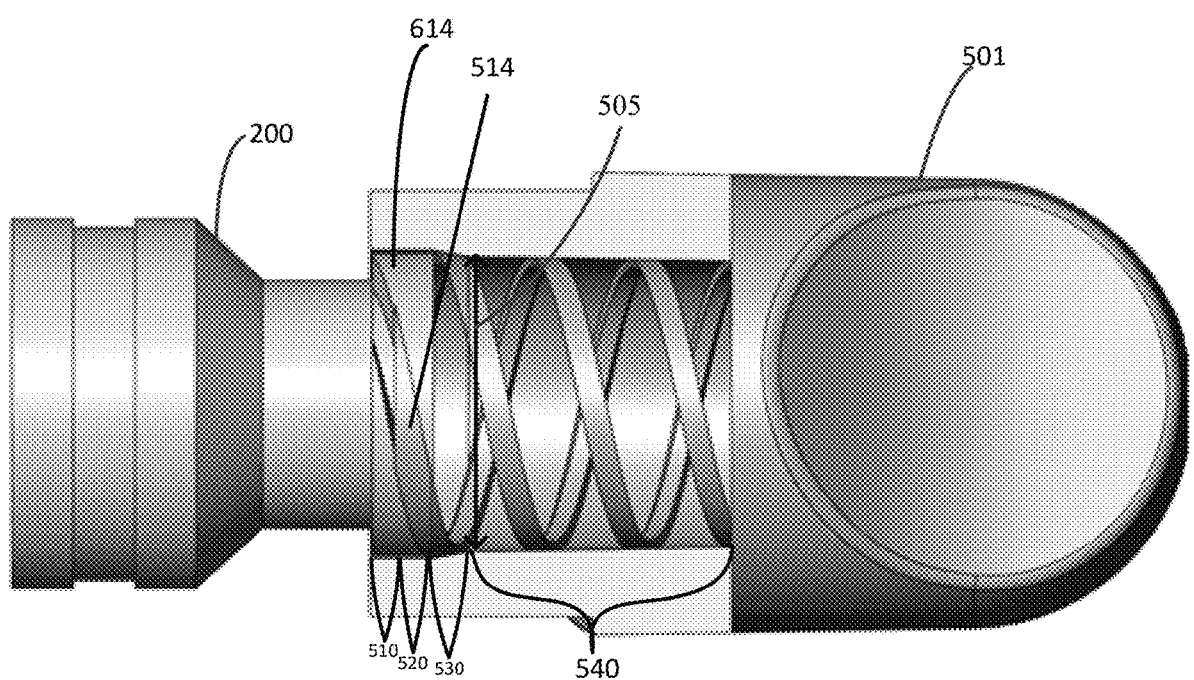
FIG. 7 shows a partial cut-away view of the arrangement shown in FIG. 6, where a preferred embodiment of the invention further engages the NIS.

FIG. 7 shows a partial cut-away view of a preferred embodiment of the cap of the present invention where the cap 501 threadingly engages the NIS 200. The threads 614 of the NIS have begun to engage with the threads 514 of the cap 501. As can be seen, the NIS 200 has entered the free running zone 520. However, the NIS 200 has not yet entered the transition zone 530 nor the main bore 540. The free running zone 520 allows the NIS 200 to begin engagement of the threads 514 without resistance. As the NIS 200 is advanced further, it passes through the transition zone 530 and may eventually pass into the main bore 540. The interaction of the NIS 200 with the second diameter 505 in the main bore 540 may provide the interference fit.

Figure 8:
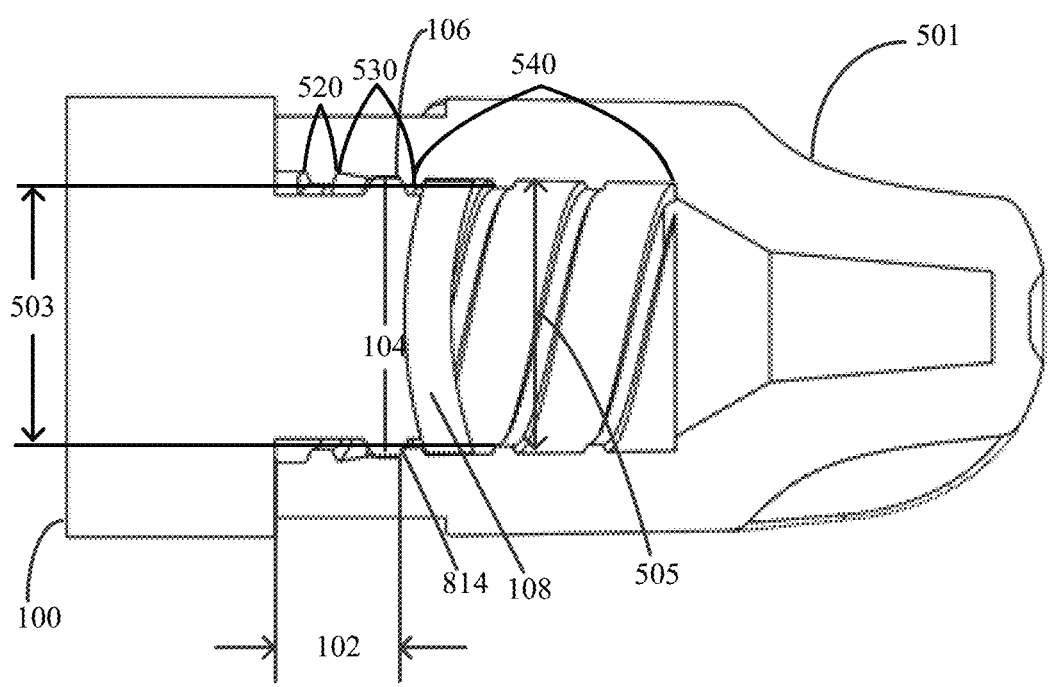
FIG. 8 shows a sectional view of a preferred embodiment of the invention interacting with Q-Syte Needleless Injection Site.

FIG. 8 shows a sectional view of a preferred embodiment of the invention interacting with prior-art Q-Syte NIS 100. In the design presented herein, the securement is provided by slight interference between an inner diameter of the cap 501, and an outer diameter of the NIS 100. The challenge is providing a fit which has sufficient interference to provide security in use, but not so much interference as to be difficult to install. The present invention provides a secure fit which does not allow the cap 501 to fall off the NIS 100 during normal use and wear, prevents damage to the septum 108 of the Becton Dickinson Q-Syte NIS 100, and provides the above functions on a range of NIS brands and models. In some embodiments, the interference fit between the Q-Syte NIS 100 and the cap 501 may be provided in the transition zone 530. Because septum 108 extends beyond the Q-syte NIS 100 body, it may be folded over and caught between the cap threads 514 and the Q-syte NIS threads 814. In some embodiments, to prevent damage to septum 108, the diameter of the cap threads 514 in the transition zone 530 and/or free running zone 520 may be increased. However, in some embodiments, the minor diameter 503 of the cap threads 514 within the main bore 540 may remain the same.

Figure 9:
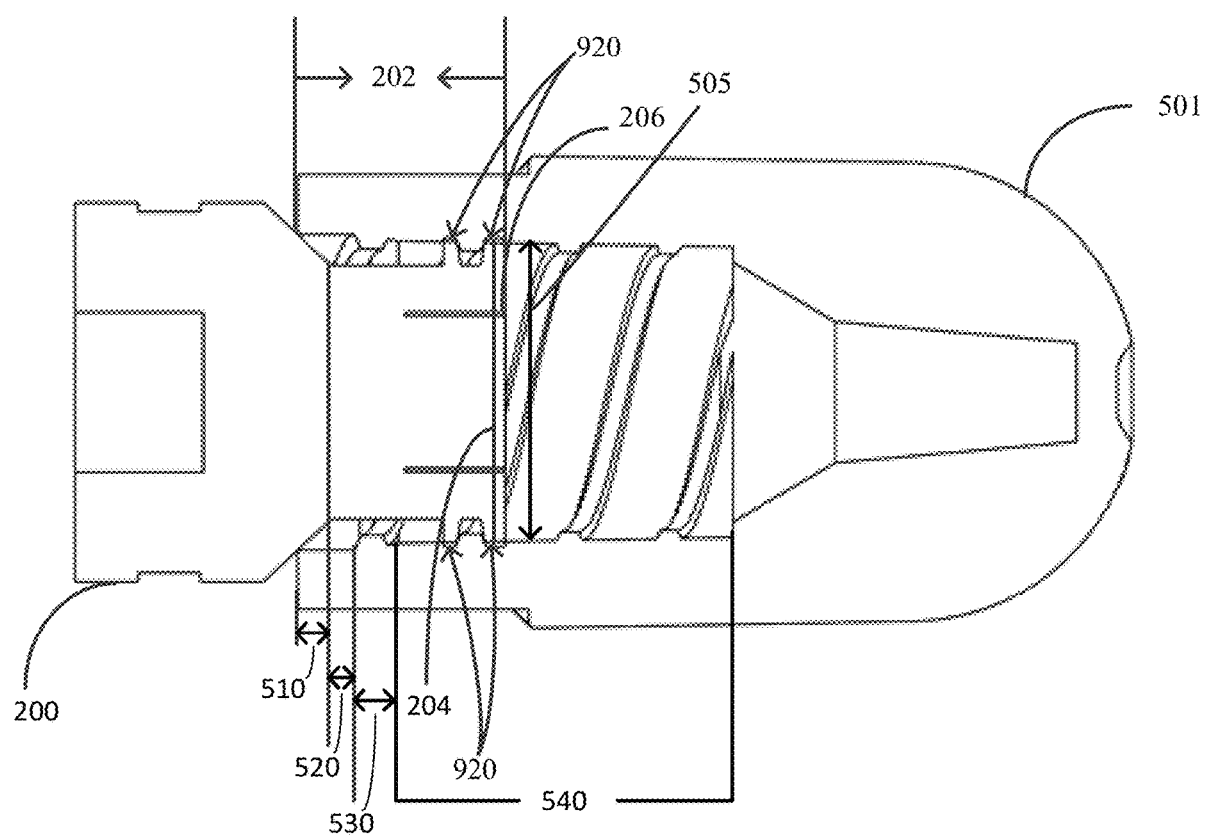
FIG. 9 shows a sectional view of a preferred embodiment of the invention interacting with SmartSite Needleless Injection Site.

FIG. 9 shows a sectional view of a preferred embodiment of the invention interacting with prior-art SmartSite NIS 200. As mentioned previously, the interference fit may come from the inner diameter of the cap 501 and the outer diameter of the NIS 200. Specifically, the interference fit between the major thread diameter 204 of the NIS 200 and the cap major thread diameter 505 may provide a secure fit which may prevent the cap 501 from falling off of the NIS 200. In some embodiments, and with some NISs, there may be more than one point of thread interference 920. For example, there may be many points of radial thread locking interference 920. In some embodiments, the interference 920 between the inner diameter of the cap 501 and the outer diameter 204 of the NIS 200 may be in the main bore 540 and in the transition zone 530. For example, in some embodiments, the thread locking interference 920 may span from the transition zone 530 to the main bore 540. Some other embodiments may have the have the zone of thread interference 920 in just the main bore 540. It should be understood that different embodiments of the invention may have radial thread interference with medical connectors in different zones and/or zone combinations based on the dimensions of the particular medical connector.

Figure 10:
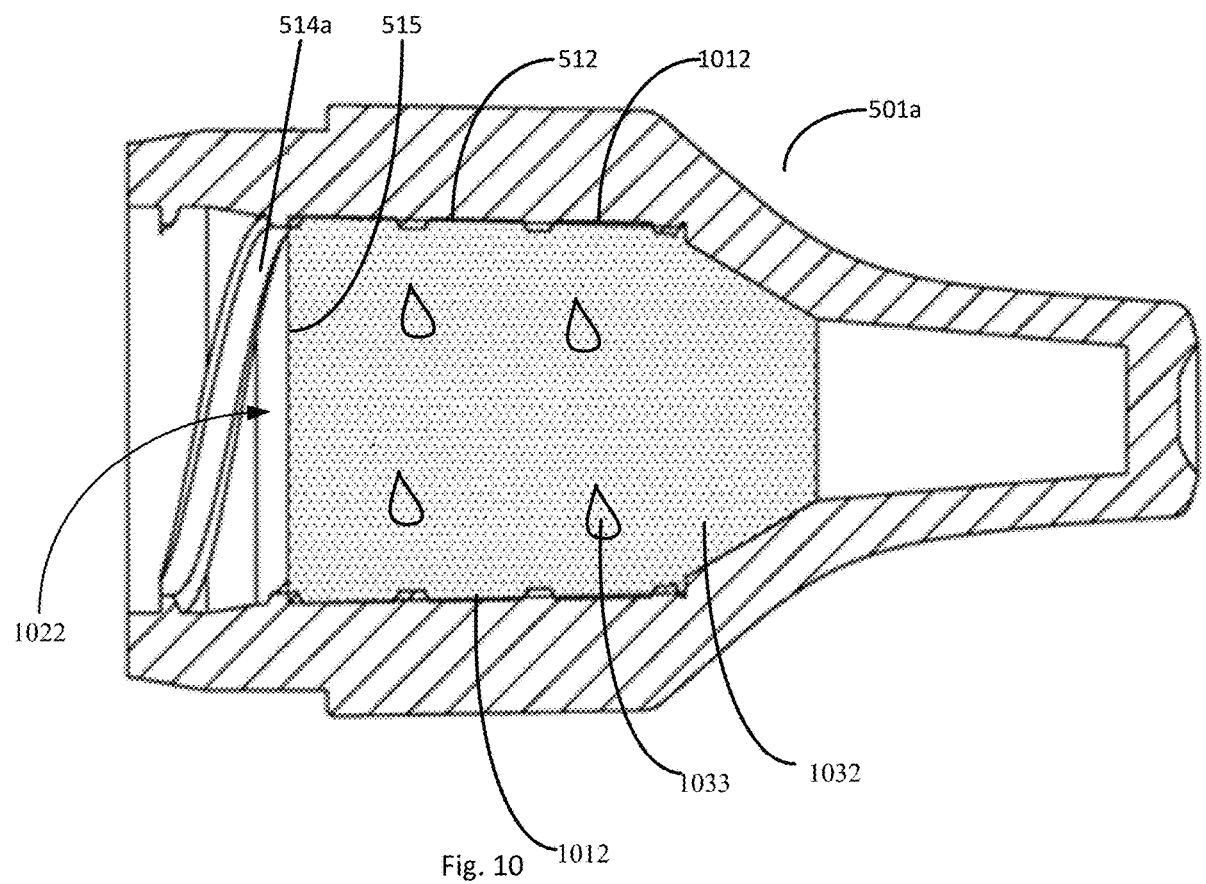
FIG. 10 shows a sectional view of a preferred embodiment of the invention having an absorbent pad.

FIG. 10 is a sectional view of a disinfecting cap 501a with an absorbent pad 1032 for holding an antiseptic 1033, such as isopropyl alcohol or another disinfectant. When capping disconnected medical connectors, it can be desirable to do more than merely cover the connectors. For example, an absorbent pad, such as pad 1032, seen in FIG. 10, may optionally be included within the cap 501a (e.g., within the disinfection chamber 1022), such as by displacing pad 1032 into cap 501a. Pad 1032 is seen disposed in cap 501a in FIG. 10. An antiseptic 1033 can also be disposed within cap 501a. The antiseptic 1033 can be in liquid or solid form. For example, alcohol or another stable liquid antiseptic 1033 may be added from a container to be received within, wet, soak, or saturate the pad 1032 to a predetermined concentration level. The pad 1032 will substantially remain at the predetermined concentration level due to the exterior seals provided for the cap 501*a*. Alternatively, or additionally, the pad 1032 may receive or be impregnated with a dry antiseptic 1033, such as, for example, chlorhexidine gluconate.

The pad 1032 can be formed of a deformable, resilient material. The pad 1032 can be compressed within the cap 501*a* when the cap 501*a* is coupled to a medical connector, such as a needleless injection site. More specifically, during the connection of the cap 501*a* to a medical connector, the cap 501*a* and the pad 1032 rotate relative to an opening edge of the medical connector, thereby drawing the medical connector into the cap 501*a*. The rotation of the cap 501*a* causes the pad 1032 to wipe or scrub the opening edge of the medical connector. Pad 1032 and any antiseptic 1033 disposed within cap 501*a* can thus cleanse and disinfect the opening edges of the medical connector. The pad 1032 can also be formed such that when a medical connector is coupled to the cap 501*a*, the pad 1032 is deformed such that the pad 1032 extends around the opening edges and/or threads of the medical connector. For example, the pad 1032 can be formed such that as the cap 501*a* is twisted onto the medical connector, the pad 1032 deforms around the threads and/or the opening edges of the medical connector, thereby scrubbing the threads and/or the opening edge of the medical connector. Further, the pad 1032 can expand to its original shape when the medical connector is removed from the cap 501*a*.

The pad 1032 can also provide additional functionality when a liquid antiseptic 1033 is disposed within the cap 501*a*. In particular, the pad 1032 acts as a sponge to absorb or release the liquid antiseptic within the cap 501*a*. More specifically, when the pad 1032 is compressed by the medical connector, pad 1032 releases at least a portion of the antiseptic 1033 so that the antiseptic 1033 can be transferred to the opening edges of the medical connector. Conversely, when a medical connector is disconnected from the cap 501*a*, the pad 1032 expands and absorbs excess antiseptic 1033 so that the antiseptic 1033 does not drip or spill out of the cap 501*a*.

In some embodiments, the pad 1032 can be deformable, and can also be configured to retain an antiseptic 1033. In some further embodiments, the pad 1032 can be resiliently deformable. For example, the pad 1032 can comprise any suitable sponge-like material, such as an elastomeric foam, any open-cell foam, felt, or non-woven fiber matrix, and can be configured to conform to the contours of a portion of a medical connector that is introduced into the disinfection chamber 1022. The pad 1032 can also comprise any closed-cell foam, as well as a solid elastomeric foam such as silicone or the like.

The pad 1032 can have a series or network of openings or spaces therein that can retain the antiseptic 1033 when the pad 1032 is in an expanded state. For example, the antiseptic 1033 can be received within, occupy, fill (or partially fill), wet, soak, or saturate at least a fraction of the pad 1032, or stated otherwise, can fill the pad 1032 to a given concentration level. Compression of the pad 1032 can cause antiseptic 1033 to egress from the pad 1032 so as to contact the medical connector. Resilient expansion of the foam upon removal of a compressive force can allow the pad 1032 to soak up or absorb at least some of the antiseptic 1033 that had previously been forced from the pad 1032. In some embodiments, the antiseptic 1033 can comprise any liquid antiseptic, such as alcohol (e.g., isopropyl alcohol) at various concentrations ranging from 50-90%, ethanol at various concentrations ranging from 50-95%, and combinations of any alcohols with any antiseptics, or a dry material, such as chlorhexidine, ethylenediaminetetraacetic acid (EDTA), Iodaphors, or any suitable combination thereof. Accordingly, although the antiseptic 1033 is schematically depicted in as a series of droplets, the antiseptic 1033 is not necessarily liquid and may fill the pad 1032 to a greater or lesser extent than what is shown. In the illustrated embodiment, when the disinfection chamber 1022 is in a sealed state (e.g., in its pre-use condition), the pad 1032 may be in a relaxed, expanded, or uncompressed state in a longitudinal direction. It is noted that the pad 1032 may be uncompressed in one or more dimensions, yet compressed in one or more other dimensions, when in the pre-use state. For example, the pad 1032 can be expanded or in a relaxed state in a longitudinal direction, yet compressed radially inwardly via the sidewall 1012, when the cap 501*a* is in the pre-use state. The pad 1032 may be uncompressed in the longitudinal direction when the cap 501*a* does is not interacting with the connection interface of the medical connector.

In the illustrated embodiment, the pad 1032 is substantially cylindrical and defines an outer diameter that may be approximately the same size as an inner diameter of the threads 514*a*. In other embodiments, the outer diameter of the pad 1032 can be larger than the inner diameter of the threads 514*a* so as to be radially compressed and held tighter within the disinfection chamber 1022. In further embodiments, the pad 1032 can include threading that projects radially inwardly and that is complementary to the threads 514*a* to thereby secure the pad 1032 within the chamber 1022.

When the cap 501*a* is coupled with the medical connector, the coupling action can bring a portion of the medical connector into contact with the pad 1032 and can allow the pad 1032 to wipe or scrub the medical connector, as described above. Likewise, the antiseptic 1033 can be forced into contact with the medical connector during the coupling phase and can remain in contact with the medical connector, while the cap 501*a* is coupled with the medical connector. The connection interface can cooperate with a connection interface of the medical connector to maintain the cap 501*a* in an attached configuration relative to the connector. Moreover, the connection interface can couple with the medical connector, such as via complementary threading, so as to prevent antiseptic from leaking from the disinfection chamber 1022.

In some embodiments, such as where the pad 1032 is formed of a material that is not fully elastically resilient or that requires a relatively long relaxation time in which to transition from a compressed state to a relaxed or uncompressed state (e.g., in a longitudinal direction), pre-use storage in the relaxed or uncompressed state in at least one dimension can preserve or enhance the cleaning, scrubbing, or disinfection properties of the pad 1032. For example, as the pad 1032 is coupled with the medical connector (e.g., the NIS 400 of FIG. 4), an end of the medical connector can come into contact with a proximal surface 515 of the pad 1032. Further advancement of the pad 1032 onto the medical connector can cause the pad 1032 to deform to complement a contour of the end of the medical connector as the pad 1032 is compressed, which can permit a relatively tight or continuous contact between the pad 1032 and the medical connector. In the illustrated embodiment, the pad 1032 is rotated relative to the medical connector, as it is advanced onto the medical connector. This rotational motion causes the contoured surface of the pad 1032 to rub the medical connector. In certain embodiments, increasingly greater compression of the pad 1032 yields increasingly stronger rubbing of the medical connector, coupled with greater amounts of the antiseptic 1033 being expelled from the pad 1032. Accordingly, when the pad 1032 is uncompressed in at least one dimension (e.g., in a longitudinal direction) in a pre-use state, and thus is not plastically deformed or is not subject to time-consuming elastic recovery from pre-compression, the pad 1032 can be in disinfecting contact with the medical connector for a relatively greater portion of the coupling procedure. In some embodiments, a practitioner can more quickly couple the pad 1032 to the medical connector, as there is no need to first wait for the pad 1032 to relax to an uncompressed or expanded state to achieve better disinfection of the medical connector.

Various parameters can be adjusted to determine the amount of antiseptic 1033 that is expelled from the pad 1032 when the pad 1032 is coupled with a medical connector. For example, the depth to which the medical connector is received within the disinfection chamber 1022, the concentration of antiseptic 1033 within the pad 1032, and/or other parameters can be altered. In various embodiments, no less than about ¼, no less than about ⅓, no less than about ½, no less than about ⅔, or no less than about ¾ of the antiseptic 1033 is expelled from the pad 1032 when the pad 1032 is coupled with a medical connector. In some embodiments, all, or substantially all, of the antiseptic 1033 is expelled from the pad 1032.

Figure 11:
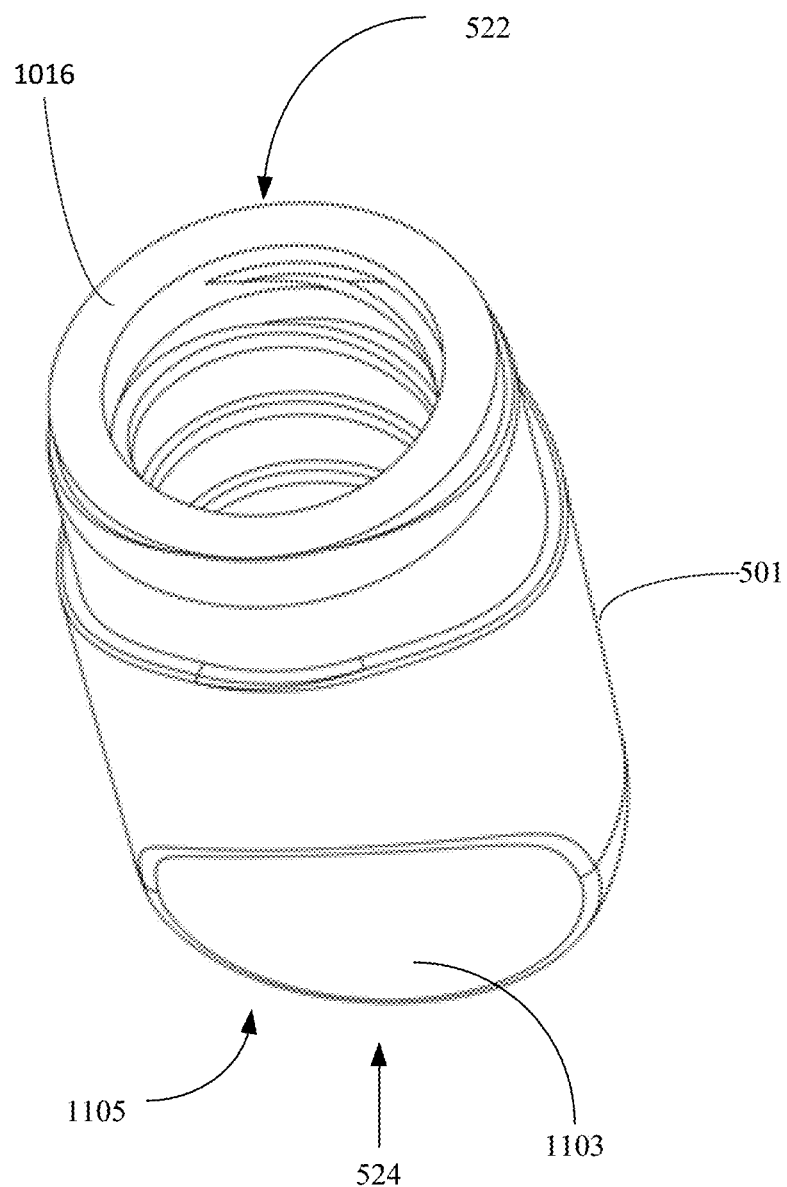
FIG. 11 shows a perspective end view of a preferred embodiment of the invention.

FIG. 11 is a perspective end view of the disinfecting cap 501 shown in FIG. 5. As discussed, the cap 501 can be coupled and decoupled with a medical connector by a user (e.g., medical professional). The cap 501 can include features to aid in such a decoupling action and/or in the coupling of the cap 501 with the respective medical connectors. For example, in the illustrated embodiment, the cap 501 may include a graspable end 524. The graspable end 524 may have a gripping portion 1105. The gripping portion 1105 can have gripping features 1103. The gripping features 1103 can comprise longitudinally extending tapered portions that taper from a relatively wide width near the openable end 522 to a narrower width at or near a gripping portion 1105. In some embodiments, the cap 501 may have a sealing surface 1016 to which a cover may be applied to seal the cap 501.

Figure 12:
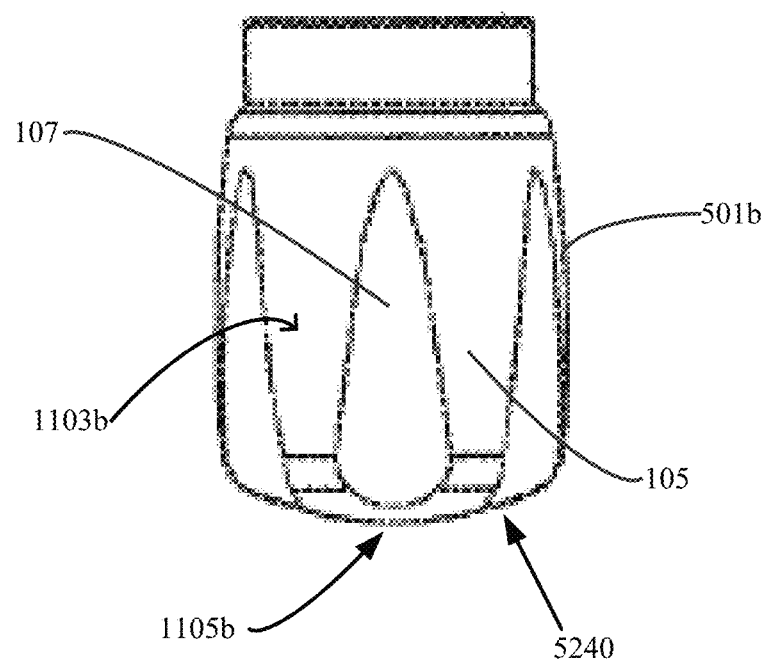
FIG. 12 shows a side view of an alternative embodiment of the invention.

FIG. 12 shows a side view of an alternative embodiment of the disinfecting cap 501b. Alternatively, or additionally, gripping portion 1105b may have extending lands or ridges 105 that taper from a relatively wide width near the interface of the cap 501b with the medical connector to a narrower width at or near a graspable end 524b of the cap 501b. The gripping features 1103b can further include longitudinally extending depressions or grooves 107 between adjacent ridges 105. For example, the grooves 107 can extend radially inwardly from an outer surface of the cap 501b that comprises the ridges 105, and the grooves 107 can also commence at a position near the interface and can grow wider and deeper toward an outer end of the cap 501b. The gripping features 1103b can further include longitudinally extending bumps or protrusions between adjacent ridges 105. The protrusions can extend radially outwardly from an outer surface of the cap 501b that comprises the ridges 105, and the protrusions can also commence at a position near the interface and can grow wider and taller toward the graspable end 524b of the cap 501b. The uneven surfaces provided by the ridges 105 and the grooves 107 or protrusions can facilitate rotational movement of the cap 501b (e.g., rotational movement relative to each other), which can aid in decoupling and/or securing the cap 501b to medical connectors. For example, the uneven surfaces may be easily gripped by the fingertips of a medical practitioner.

Figure 13:
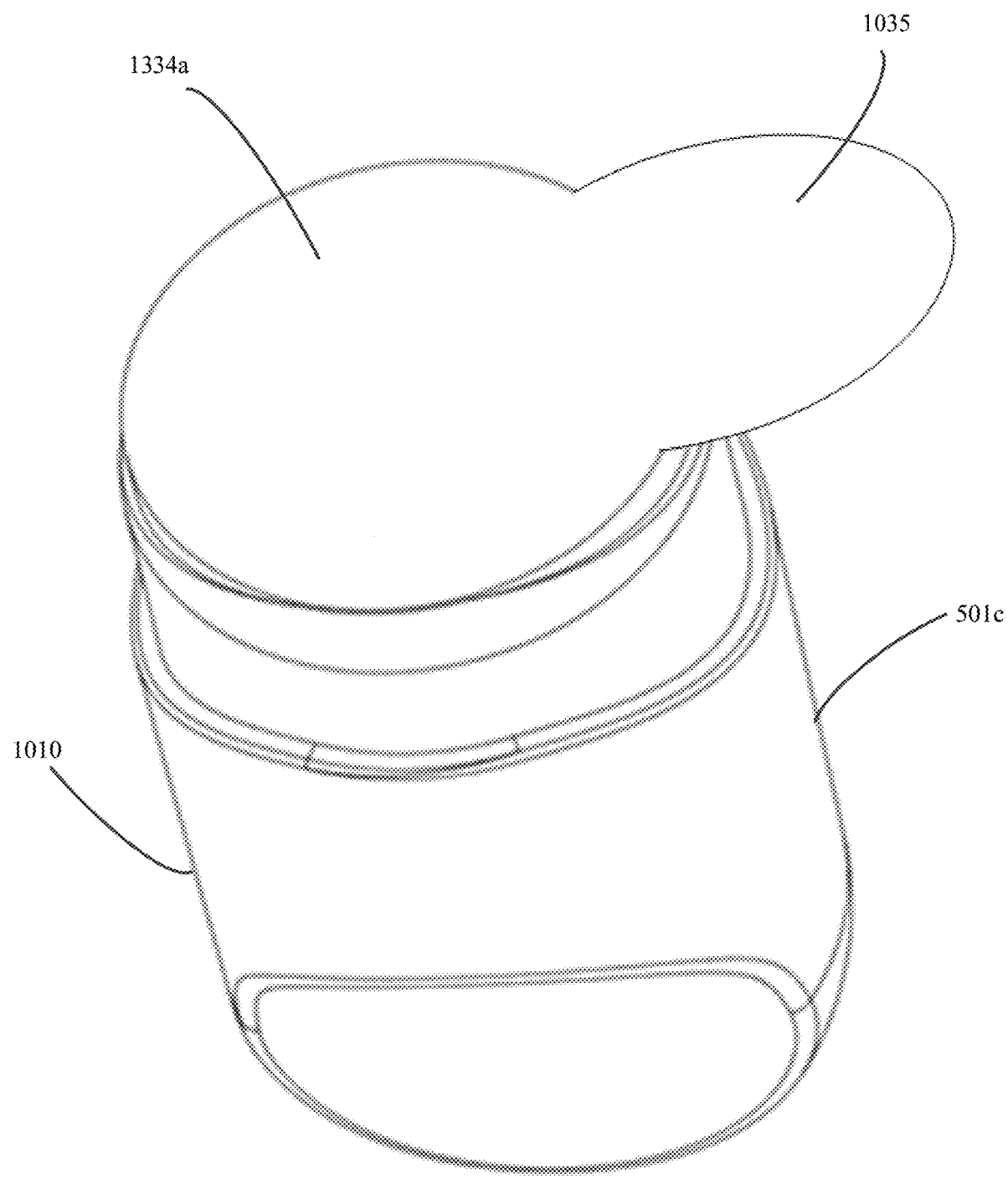
FIG. 13 shows a perspective end view of a preferred embodiment of the invention with a cover.

FIG. 13 shows a perspective end view of an embodiment of a cap 501c with a cover according to the present invention. The disinfection chamber 1022 can be sealed at the sealing surface via a cover 1334a that can span an open end of the disinfection chamber 1022. The cover 1334a can be secured to the housing 1010 in any suitable manner, such as, for example, via an adhesive. Preferably, the cover 1334a can be readily removed by a practitioner. For example, in some embodiments, the cover 1334a can include a tab 1035 and a practitioner can readily remove the cover 1334a by holding the housing 1010 in one hand and pulling the tab 1035 away from the housing 1010 with the other hand. The removable cover 1334a can be formed of any suitable material, such as, for example, an impervious pliable material (e.g., foil, plastic, metallized-surface mylar, and the like). The cover 1334a can provide a hermetic seal that can assist in maintaining the sterility of the cap 501c prior to use of the cap 501c and/or can prevent evaporative loss of antiseptic from the cap 501c.

Figure 14:
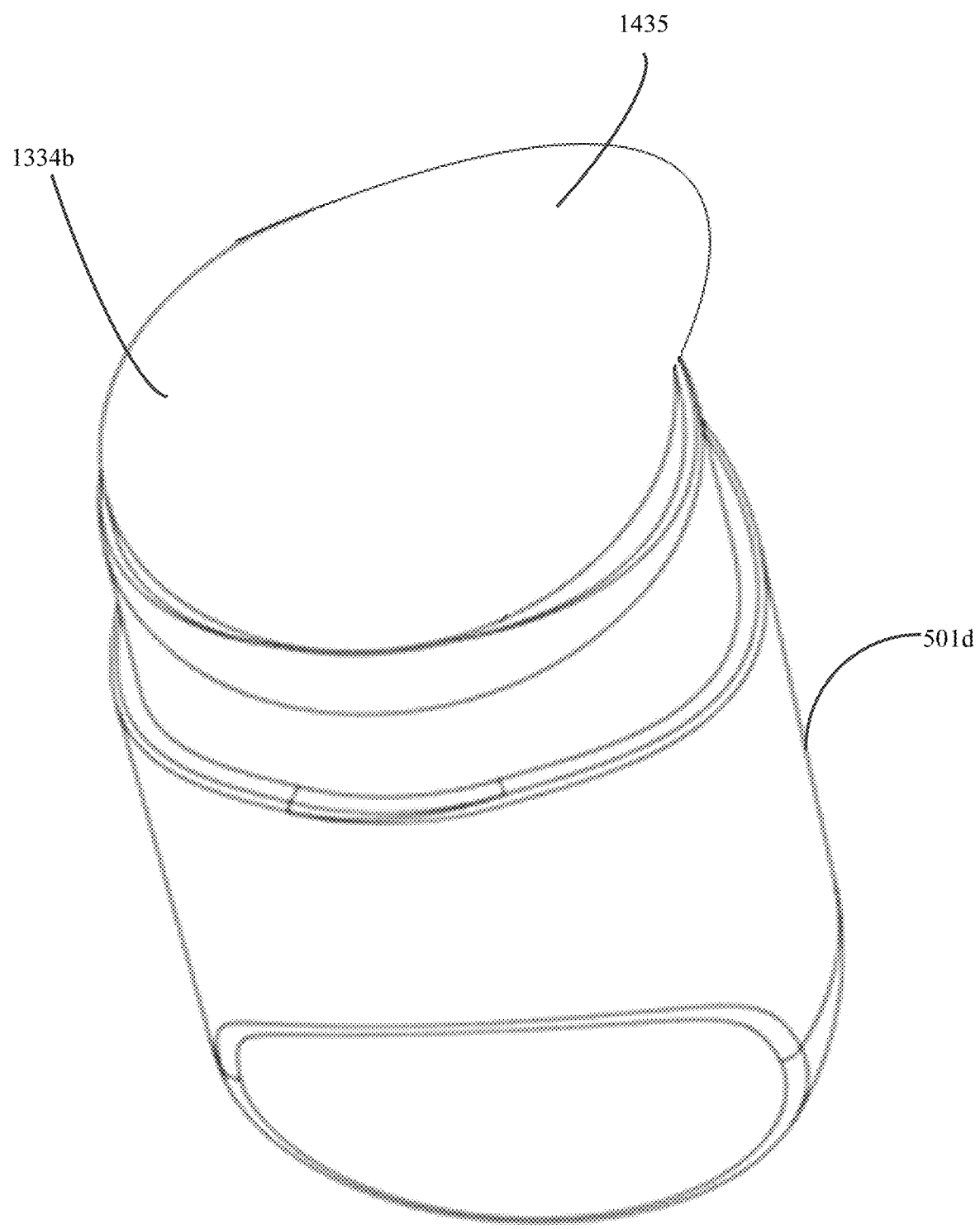
FIG. 14 shows a perspective end view of an alternative embodiment of the invention with a cover.

FIG. 14 shows a perspective end view of an alternative embodiment of a cap 501d with a cover 1334b according to the present invention. As opposed to FIG. 13, which had a cover 1334a with a tab 1035 protruding from the main body of the cover, the cover in FIG. 14 is designed to smoothly integrate with the main body of the cover 1334b. In the embodiment, the cover 1334b smoothly transitions into the tab 1435 along the sealing surface. The cover 1334b may have an egg-like shape and may distribute pressure more evenly when removed, thereby allowing even and complete removal of the cover 1334b without tearing the cover 1334b or leaving any remnants of the cover 1334b.

Figure 15:
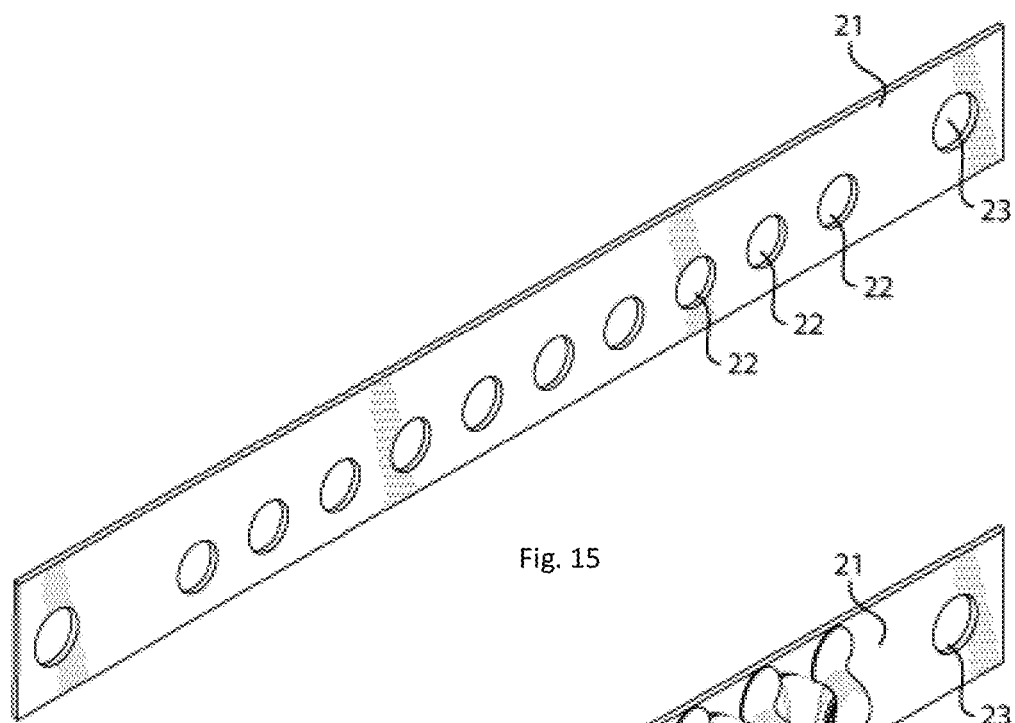
FIG. 15 is a perspective view of a carrier for use in connection with an embodiment of the present invention.

FIG. 15 is a perspective view of a carrier 21 for use in connection with an embodiment of the present invention. The carrier 21 includes a sheet that may be made of any suitable material. Suitable materials may be polymeric or composite polymeric materials, such as a polyolefin, styrene, polyethylene terephthalate (PET, including Mylar), polyvinyl chloride (PVC), or polyurethane. Of the polyolefins, low or high density polyethylene may be suitable, as well as polypropylene. Although the sheet may desirably be flexible, in other applications, a rigid sheet may also be employed for the carrier.

The carrier 21 includes at least one mounting hole 23, located to facilitate mounting of the carrier at one end, and may optionally include a pair of mounting holes 23 at each end or any desired number of mounting holes 23. One of the mounting holes 23 may be used, for example, to hang the carrier 21 on a hook or other member protruding from an IV pole. Alternatively, a pair of mounting holes 23 may be used simultaneously to mount the carrier 21 in an approximately horizontal orientation. The carrier 21 also includes an array of holes 22 for receiving therein a corresponding population of medical connector caps, in a manner discussed in further detail below.

Figure 16:
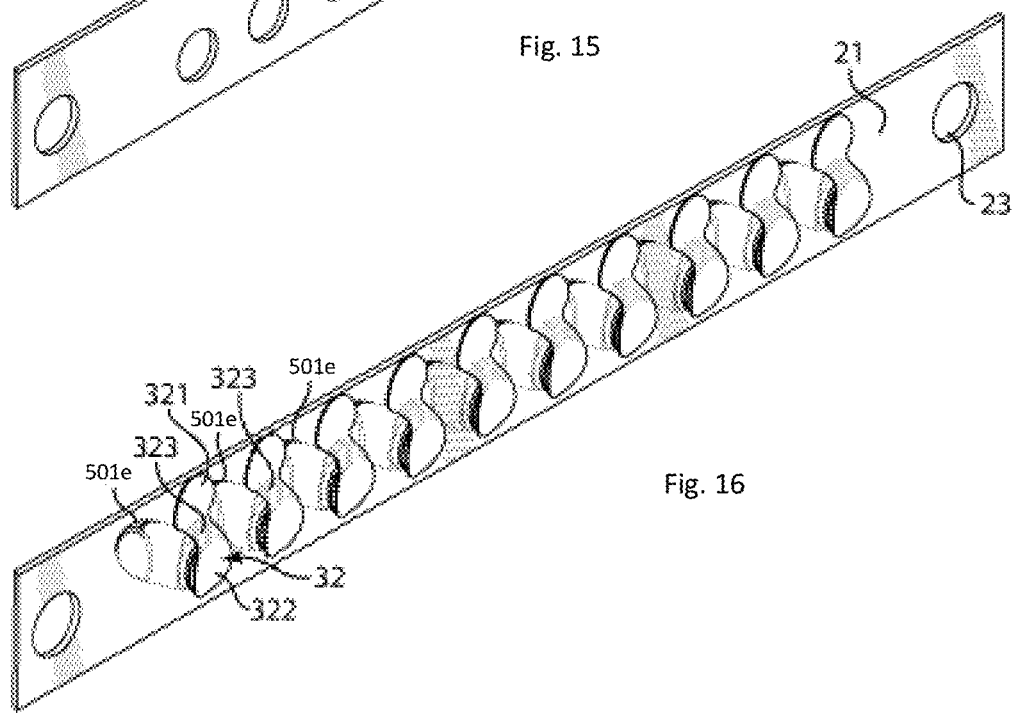
FIG. 16 is a perspective view of an assembly including the carrier of FIG. 15, as seen from the underside of the carrier, populated with medical connector caps, in accordance with an embodiment of the present invention.

FIG. 16 is a perspective view of an assembly including the carrier 21 of FIG. 2, as seen from the underside of the carrier 21, populated with medical connector caps 501e, in accordance with an embodiment of the present invention. A medical connector cap 501e resides in each hole 22 in the array of holes in the carrier 21 depicted in FIG. 15. Each hole 22 is sized to secure its corresponding cap with a friction fit, so as to mechanically stabilize the cap in relation to the carrier 21. The carrier 21 may be suitably populated with female medical connector caps. Alternatively, the carrier 21 may be suitably populated with male medical connector caps. As yet another alternative, the carrier 21 may be populated with a mixture of male and female medical connector caps. Because the dimensions of caps for male medical connectors are typically different from the dimensions of caps for female medical connectors, the size of the holes 22 will typically need to be sized according to specific medical connector cap intended to be resident therein. In an alternative embodiment, the holes 22 are configured to receive the medical connector caps without a friction fit.

In the embodiment of FIG. 16, each cap 501e has a separate sealing tab 32. The sealing tab 32 includes a cover portion 322, which sealingly covers the openable end of the cap 501e. The sealing tab also includes an overhang portion that overhangs the openable end of the cap 501e. The overhang portion is dimensioned to include a tether 323 of sufficient length that a tip 321 of the tether overlaps an adjacent portion of the carrier 21. The tip 321 is affixed to the carrier 21, so that the corresponding cap 501e is tethered to the carrier 21 by the sealing tab 32. The sealing tab may be made of metal foil or it may be a composite polymeric sheet with a metal foil layer as a barrier. In the event a composite is used for the sealing tab, it is necessary only that the foil layer should exist over the openable end of the cap 501e; no foil is needed on the tether 323 or the tip 321 of the tether, although optionally the entire tab may include the foil layer. The sealing tab 32 may be affixed to the openable end of the cap 501e and to the carrier 21 by glue, UV adhesive, mechanical means, or by thermal bonding.

Figure 17:
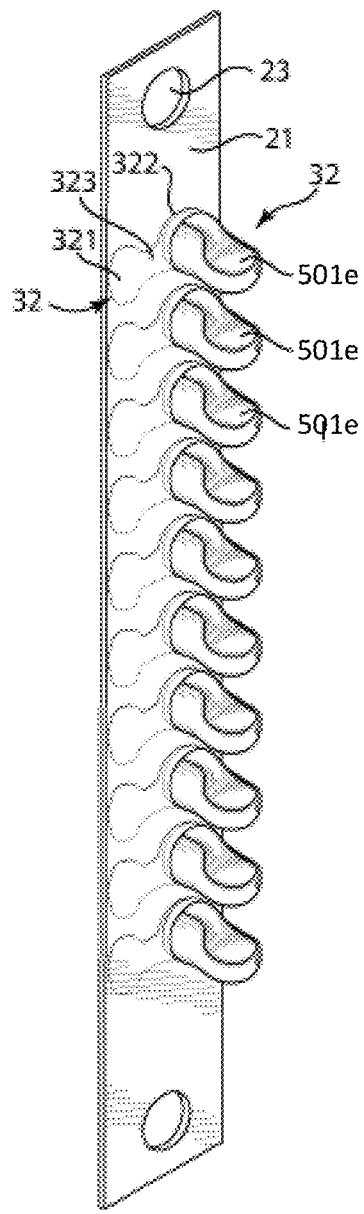
FIG. 17 is another perspective view of the assembly of FIG. 16, this time as seen from the upper side of the carrier.

FIG. 17 is another perspective view of the assembly of FIG. 16, this time as seen from the upper side of the carrier.

Figure 18:
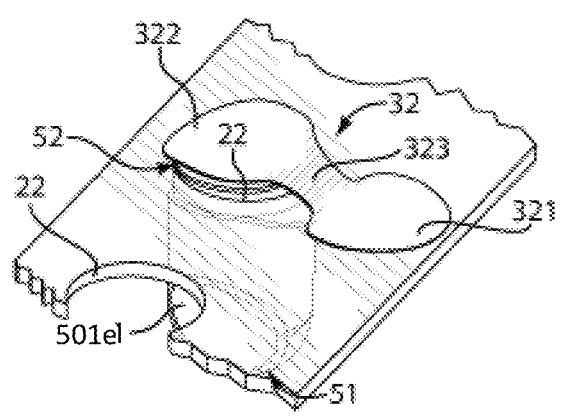
FIG. 18 is a perspective view from the underside of the assembly of FIG. 16, providing detail with respect to a single connector cap of the assembly.

FIG. 18 is a perspective view from the underside of the assembly of FIG. 16, providing detail with respect to a single connector cap of the assembly.

Figure 19:
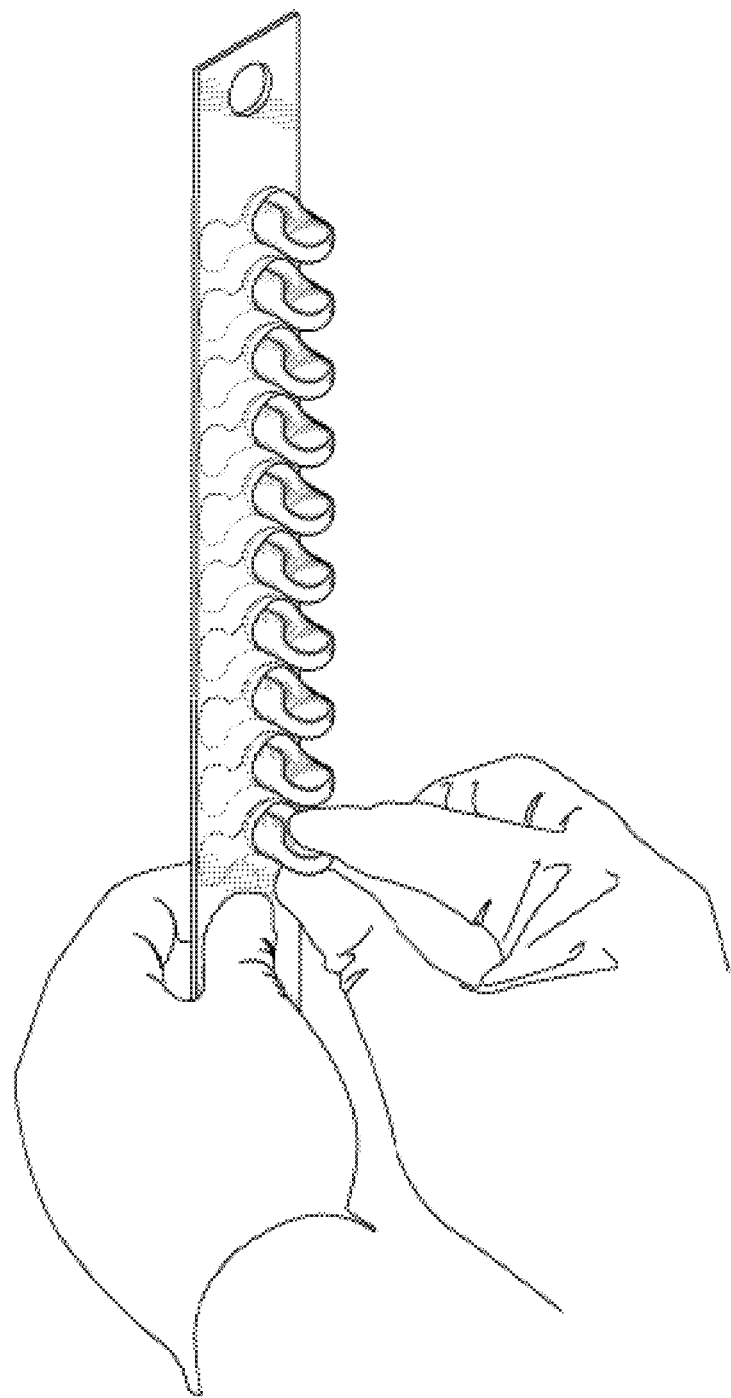
FIGS. 19-21 are a series of perspective views showing how the assembly can be used to prepare a medical connector cap for use.
Figure 20:
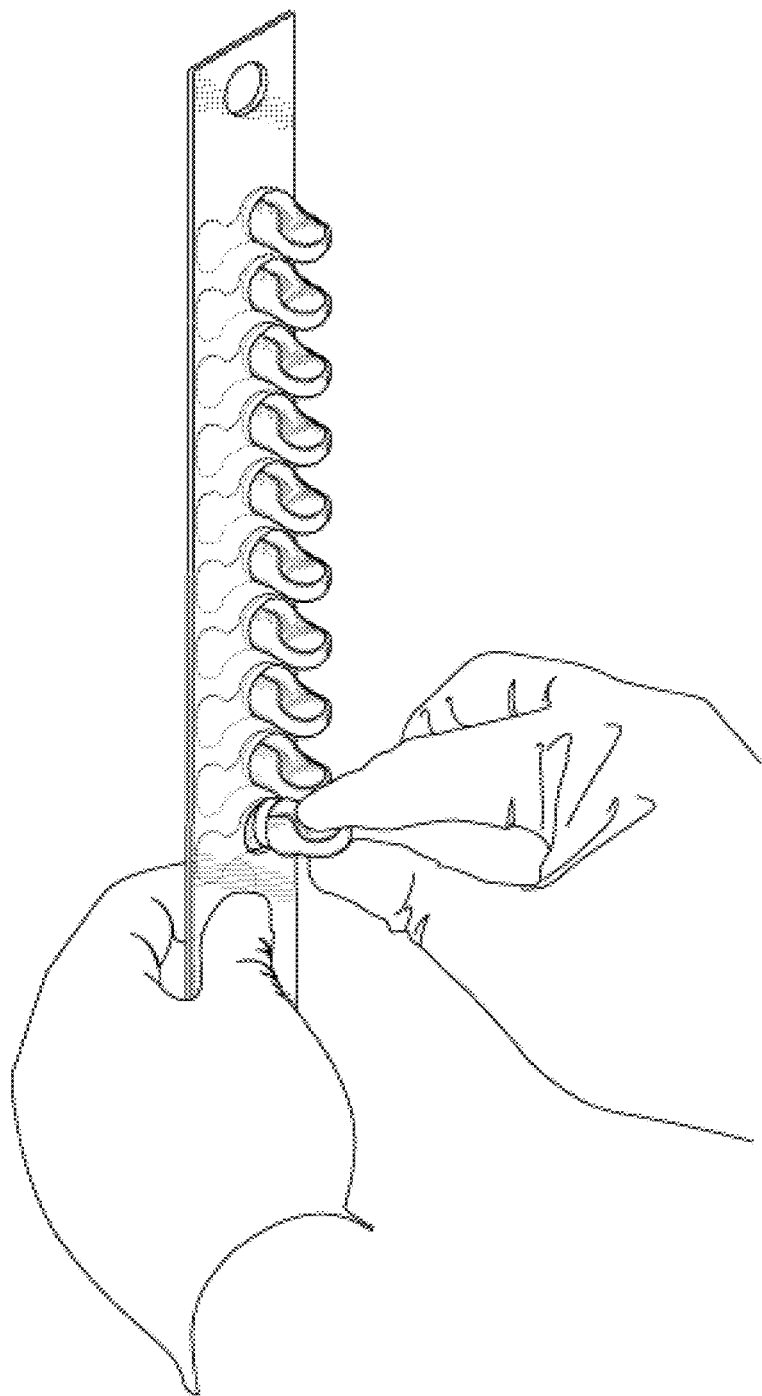
Figure 21:
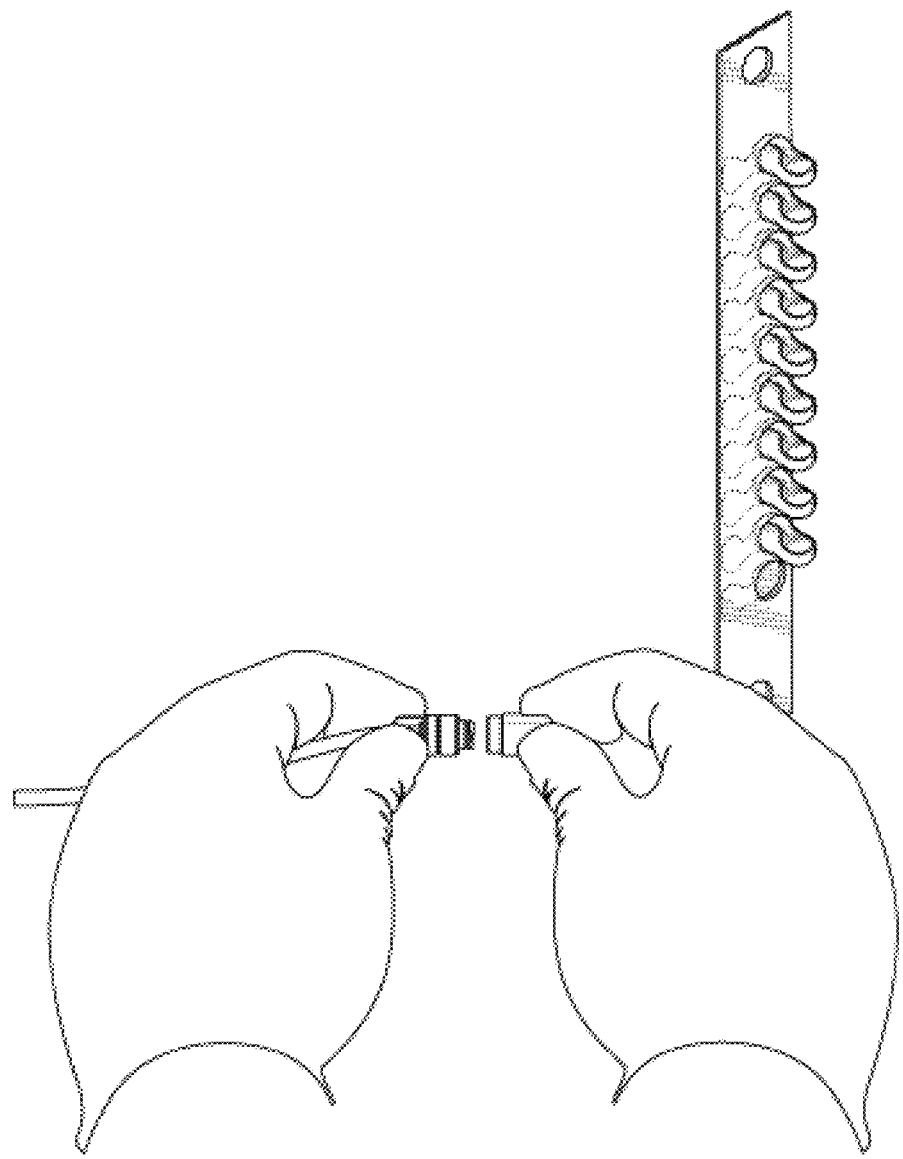

FIGS. 19-21 are a series of perspective views showing how the assembly can be used to prepare a medical connector cap for use. In FIG. 19, the user is seen to have grasped with one hand the graspable end of the connector cap while with another hand to have grasped the carrier.

In FIG. 20, the user has partially removed the cap from its corresponding hole 22 in the carrier 21 and caused some of the cover portion 322 of the sealing tab 32 to be removed from the openable end of the cap. The tether 323 and its tip 321 keep the sealing tab 32 affixed to the carrier 21.

In FIG. 21, the user has completely removed the cap from its corresponding hole in the carrier and caused the cover portion of the sealing tab to be removed from the openable end of the cap. The tether 323 and its tip 321 continue to keep the sealing tab 32 affixed to the carrier 21. In FIG. 21, the user is seen to be ready to place the cap—here a cap for female medical connector, in particular, for a needleless injection site—on the corresponding medical connector.

As described in connection with FIG. 16, embodiments of the present invention are equally applicable to caps for male connectors, so FIGS. 19-21 might have shown the user as having removed a cap for a male connector from an appropriately populated carrier 21, and being ready to place the male cap on a male medical connector.

FIGS. 19-21 show that the user may prepare a medical connector cap for use, with a single gesture that removes the medical connector cap from the carrier 21 and also removes the sealing tab 32 from the connector cap.

Although we have just shown how as part of the single gesture the sealing tab 32 may be removed from the connector cap, the sealing tab (and the tether 323 and tip 321) may be configured so that when a user prepares the selected one of the caps for use, a user can choose to manipulate the cap in relation to the carrier (for example, by twisting it in place) so as to break the tether, and thereafter remove the cap from its corresponding hole, while leaving the cover portion of the sealing tab to sealingly cover the openable end of the cap. In this manner, a user may remove the cover portion at a desired time after removing the cap from its corresponding hole.

The embodiments of the invention described above are intended to be merely exemplary; numerous variations and modifications will be apparent to those skilled in the art. All such variations and modifications are intended to be within the scope of the present invention as defined in any appended claims.

While specific parameter values may be recited for disclosed embodiments, within the scope of the invention, the values of all of parameters may vary over wide ranges to suit different applications.

While the invention is described through the above-described exemplary embodiments, modifications to, and variations of, the illustrated embodiments may be made without departing from the inventive concepts disclosed herein. Furthermore, disclosed aspects, or portions thereof, may be combined in ways not listed above and/or not explicitly claimed. Accordingly, the invention should not be viewed as being limited to the disclosed embodiments.

We claim:

1. A female-disinfecting cap for threadingly accepting a needleless injection site and applying an antiseptic agent to the needleless injection site, the female disinfecting cap comprising:

a female-disinfecting cap body having an inner sidewall defining a chamber having an opening for accepting the needleless injection site, the inner sidewall having:

a piloting zone devoid of threads and immediately adjacent the opening, the piloting zone having a first diameter, an initial threading zone immediately adjacent the piloting zone, the initial threading zone having the first diameter, a transition zone immediately adjacent the initial threading zone, the transition zone having a first transitioning diameter according to a first taper, and a main zone immediately adjacent the transition zone, the main zone having a second transitioning diameter according to a second taper that is different than the first taper; and an absorbent material for holding the antiseptic agent disposed in the chamber, wherein a pair of threads protrude from the inner sidewall and extend from the initial threading zone, through the transition zone and into the main zone, but do not extend into the piloting zone, and wherein the pair of threads encircle the inner sidewall of the main zone more than once and have a constant diameter, wherein the first transitioning diameter changes from the first diameter, at the point where the transition zone contacts the initial threading zone, to a second diameter at a point where the transition zone contacts the main zone, wherein the second diameter is less than the first diameter, wherein the pair of threads of the initial threading zone are spaced from one another effective to engage a thread of the needleless injection site therebetween, wherein the initial threading zone threadingly engages proximal threads of the needleless injection site, wherein the second diameter is sized to provide an interference fit between the inner sidewall and a thread of multiple needleless injection sites of varying size, upon placement of the female-disinfecting cap on each respective needleless injection site of the multiple needleless injection sites of varying size, and wherein the interference fit is configured to provide a resistance to rotation of the cap when coupled to one of multiple potential needleless injection sites of varying size.

2. A female-disinfecting cap according to claim 1, wherein the first diameter is between 0.31 inches and 0.32 inches inclusive.

3. A female-disinfecting cap according to claim 2, wherein the first diameter is between 0.314 inches and 0.316 inches inclusive.

4. A female-disinfecting according to claim 2, wherein the first diameter is 0.315 inches.

5. A female-disinfecting cap according to claim 4, wherein the piloting zone extends from the opening to a depth of between 0.02 inches to 0.03 inches inclusive.

6. A female-disinfecting cap according to claim 5, wherein the piloting zone extends from the opening to a depth of between 0.024 inches to 0.026 inches inclusive.

7. A female-disinfecting cap according to claim 5, wherein the piloting zone extends from the opening to a depth of 0.025 inches.

8. A female-disinfecting cap according to claim 7, wherein the first diameter extends from the opening to a depth of 0.057 inches to 0.067 inches inclusive.

9. A female-disinfecting cap according to claim 8, wherein the first diameter extends from the opening to a depth of between 0.061 inches to 0.063 inches inclusive.

10. A female-disinfecting cap according to claim 8, wherein the first diameter extends from the opening to a depth of 0.062 inches.

11. A female-disinfecting cap according to claim 1, wherein the initial threading zone extends from the end of the piloting zone to a depth of 0.057 inches to 0.067 inches inclusive from the opening.

12. A female-disinfecting cap according to claim 1, wherein the initial threading zone extends from the end of the piloting zone to a depth of 0.062 inches from the opening.

13. A female-disinfecting cap according to claim 1, wherein the transition zone begins at a depth of 0.057 inches to 0.067 inches from the opening inclusive and extends to a depth of 0.075 inches to 0.125 inches inclusive.

14. A female-disinfecting cap according to claim 1, wherein transition zone begins at a depth of 0.062 inches from the opening and extends to a depth of 0.100 inches from the opening.

15. A female-disinfecting cap according to claim 1, wherein the second diameter is between 0.298 inches and 0.302 inches inclusive such that the second diameter is configured to provide a thread locking interference with the threads of the one of multiple potential needleless injection sites of varying size.

16. A female-disinfecting cap according to claim 1, wherein the second diameter is 0.3 inches.

17. A female-disinfecting cap according to claim 1, wherein the pair of threads have a radial height sufficient to define a minor diameter of between 0.287 inches and 0.291 inches inclusive such that the pair of threads are configured to ensure engagement with the threads of the needleless injection site.

18. A female-disinfecting cap according to claim 1, wherein the pair of threads, have a radial height sufficient to define a minor diameter of not less than 0.287 inches such that the pair of threads are configured to prevent damage of a septum of the needleless injection site.

19. A female-disinfecting cap according to claim 1, wherein the pair of threads have a width, in the longitudinal direction of the female-disinfecting cap, of between 0.020 inches and 0.025 inches inclusive such that the pair of threads are configured to prevent longitudinal thread locking interference with the threads of the needleless injection site.

20. A female-disinfecting cap according to claim 1, further comprising the antiseptic agent.

21. A female-disinfecting cap according to claim 1, further comprising a gripping portion.

22. A female-disinfecting cap according to claim 1, further comprising a cover disposed over the opening of the chamber.

23. A female-disinfecting cap according to claim 22, wherein the cover comprises an impervious pliable material.

24. A female-disinfecting cap for threadingly accepting a needleless injection site and applying an antiseptic agent to the needleless injection site, the female-disinfecting cap comprising:

a female-disinfecting cap body having an inner sidewall defining a chamber having an opening for accepting the needleless injection site, wherein the cap is configured to provide an interference fit when coupled to needleless injection sites of varying size, and wherein the inner sidewall comprises:

a piloting zone devoid of threads and immediately adjacent the opening, the piloting zone including a first diameter, an initial threading zone immediately adjacent the piloting zone, the initial threading zone having the first diameter, a transition zone immediately adjacent the initial threading zone, the transition zone having a transitioning diameter, and a main zone immediately adjacent the transition zone, the main zone including a second diameter and the inner sidewall of the main zone tapers one degree relative to a longitudinal axis of the female-disinfecting cap body; and an absorbent material for holding the antiseptic agent disposed in the chamber;

an antiseptic agent held by the absorbent material; and a cover disposed over the opening of the chamber, the cover comprised of an impervious pliable material, wherein a pair of threads protrude from the inner sidewall and extend from the initial threading zone, through the transition zone and into the main zone, but do not extend into the piloting zone, wherein the second diameter is less than the first diameter, wherein the transitioning diameter changes from the first diameter, at the point where the transition zone contacts the initial threading zone, to the second diameter at the point where the transitioning zone contacts the main zone, and wherein the first diameter is between 0.31 inches and 0.32 inches inclusive, the piloting zone extends from the opening to a depth of between 0.02 inches to 0.03 inches inclusive, the first diameter extends from the opening to a depth of between 0.057 inches to 0.067 inches inclusive, the initial threading zone extends from the end of the piloting zone to a depth of between 0.057 inches to 0.067 inches inclusive from the opening, the transition zone begins at a depth of between 0.057 inches to 0.067 inches inclusive from the opening and extends to a depth of between 0.075 inches to 0.125 inches inclusive, the second diameter is between 0.298 inches and 0.302 inches inclusive such that the second diameter is configured to provide a thread locking interference with threads of the needleless injection site, the pair of threads have a radial height sufficient to define a minor threading diameter of between 0.287 inches and 0.291 inches inclusive, the pair of threads have a width, in the longitudinal direction of the female disinfecting cap, of between 0.020 inches and 0.025 inches inclusive, the pair of threads of the main zone have a plurality of turns and the second diameter is parallel to the longitudinal axis of the female-disinfecting cap, and wherein the initial threading zone threadingly engages proximal threads of the needleless injection site.

25. A female-disinfecting cap for threadingly accepting multiple potential needleless injection sites and applying an antiseptic agent to each needleless injection site, the female-disinfecting cap comprising:

female-disinfecting cap threads, a piloting portion, the piloting portion configured to align with each needleless injection site having needleless injection site threads, and allowing each needleless injection site to enter the female-disinfecting cap prior to rotational engagement of the female-disinfecting cap threads with the needleless injection site threads, a thread engagement portion having a diameter and the female-disinfecting cap threads, wherein the thread engagement portion is adjacent to the piloting portion, the diameter configured to allow engagement of and unresisted rotational threading of proximal threads of each needleless injection site with the female-disinfecting cap threads, a tapering transition portion adjacent to the thread engagement portion, the tapering transition portion having the female-disinfecting cap threads, wherein the diameter continuously narrows in the tapering transition portion according to a first taper, and the tapering transition portion is configured to provide a thread locking interference fit with a thread of the multiple potential needleless injection sites of varying size, upon placement of the female-disinfecting cap on each respective needleless injection site of the multiple potential needleless injection sites, and a tapering main bore portion adjacent to the tapering transition portion, the tapering main bore portion having the female-disinfecting cap threads, wherein the diameter of the tapering main bore portion continuously narrows in the tapering main bore portion according to a second taper that is different than the first taper and is configured to provide a thread locking interference fit with the thread of the multiple potential needleless injection sites of varying size upon placement of the female-disinfecting cap on each respective needleless injection site of the multiple potential needleless injection sites, wherein the thread locking interference fit is configured to provide a resistance to rotation of the cap when coupled to needleless injection sites of varying size, and wherein the female-disinfecting cap threads encircle the inner sidewall of the tapering main bore portion more than once and have a constant diameter and are spaced from one another effective to engage the thread of the needleless injection site therebetween.

* * * * *